(12) United States Patent
Lee et al.

(10) Patent No.: US 10,131,632 B2
(45) Date of Patent: Nov. 20, 2018

(54) DOPANT FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si, Gyeonggi-do (KR)

(72) Inventors: Sangshin Lee, Suwon-si (KR); Eun Sun Yu, Suwon-si (KR); Jun Yeob Lee, Suwon-si (KR); Yong Joo Cho, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 0 days.

(21) Appl. No.: 15/571,386

(22) PCT Filed: Oct. 26, 2015

(86) PCT No.: PCT/KR2015/011322
§ 371 (c)(1),
(2) Date: Nov. 2, 2017

(87) PCT Pub. No.: WO2016/178463
PCT Pub. Date: Nov. 10, 2016

(65) Prior Publication Data
US 2018/0215711 A1    Aug. 2, 2018

(30) Foreign Application Priority Data

May 6, 2015 (KR) ........................ 10-2015-0063365

(51) Int. Cl.
*H01L 51/00* (2006.01)
*C07D 209/82* (2006.01)
(Continued)

(52) U.S. Cl.
CPC ......... *C07D 209/82* (2013.01); *C07D 403/10* (2013.01); *C07D 403/14* (2013.01);
(Continued)

(58) Field of Classification Search
CPC ............. H01L 51/0051; H01L 51/4253; H01L 51/5016; H01L 51/5004; H01L 51/0072; H01L 27/146; H01L 27/307; H01L 31/10; C07D 209/82; C07D 403/10; C07D 403/14; C07D 413/14; C07D 417/14; C07D 209/88
See application file for complete search history.

(56) References Cited

U.S. PATENT DOCUMENTS 7,270,893 B2    9/2007  Fukuda et al.
2006/0088728 A1*  4/2006  Kwong ................ C07D 209/82
                                                      428/690

(Continued)

FOREIGN PATENT DOCUMENTS

JP    2000-021572 A    1/2000
JP    2004-071380 A    3/2004
(Continued)

*Primary Examiner* — Thanh T Nguyen
(74) *Attorney, Agent, or Firm* — Lee & Morse, P.C.

(57) ABSTRACT

The present invention relates to a dopant for an organic optoelectronic device represented by Chemical Formula 1, and to an organic optoelectronic device and a display device comprising the dopant.

16 Claims, 1 Drawing Sheet

(51) Int. Cl.

| | |
|---|---|
| *C07D 403/10* | (2006.01) |
| *C07D 403/14* | (2006.01) |
| *C07D 413/14* | (2006.01) |
| *H01L 51/50* | (2006.01) |
| *C07D 417/14* | (2006.01) |

(52) U.S. Cl.
 CPC ......... *C07D 413/14* (2013.01); *C07D 417/14* (2013.01); *H01L 51/0072* (2013.01); *H01L 51/5004* (2013.01); *H01L 51/5016* (2013.01)

(56) References Cited

U.S. PATENT DOCUMENTS

| | | | | |
|---|---|---|---|---|
| 2014/0374713 | A1* | 12/2014 | Cho | H01L 51/5004 257/40 |
| 2015/0171335 | A1* | 6/2015 | Kim | H01L 51/0058 257/40 |
| 2016/0372685 | A1* | 12/2016 | Lin | C07D 409/14 |

FOREIGN PATENT DOCUMENTS

| | | | |
|---|---|---|---|
| JP | 2004-273190 | A | 9/2004 |
| JP | 2004-311405 | A | 11/2004 |
| JP | 2005-047811 | A | 3/2005 |
| JP | 2007-227658 | A | 9/2007 |
| JP | 2011-153276 | A | 8/2011 |
| JP | 2011-256143 | A | 12/2011 |
| JP | 2012-033892 | A | 3/2012 |
| JP | 2012-126718 | A | 7/2012 |
| JP | 5619395 | B2 | 11/2014 |
| KR | 10-2011-0088427 | A | 8/2011 |
| KR | 10-2011-0088457 | A | 8/2011 |
| KR | 10-2011-0117513 | A | 10/2011 |
| KR | 10-2011-0134201 | A | 12/2011 |
| KR | 10-2014-0064655 | A | 5/2014 |
| KR | 10-2015-0010387 | A | 1/2015 |
| KR | 10-2015-0026933 | A | 3/2015 |
| KR | 10-2016-0000331 | A | 1/2016 |
| WO | WO 2011/013507 | A1 | 2/2011 |
| WO | WO 2012/002221 | A1 | 1/2012 |
| WO | WO 2013/154064 | A1 | 10/2013 |

* cited by examiner

[Fig. 1]
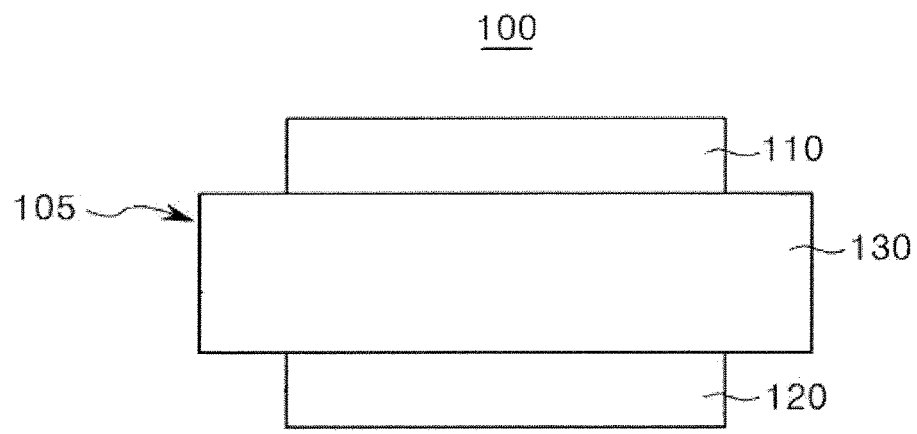
[Fig. 2]
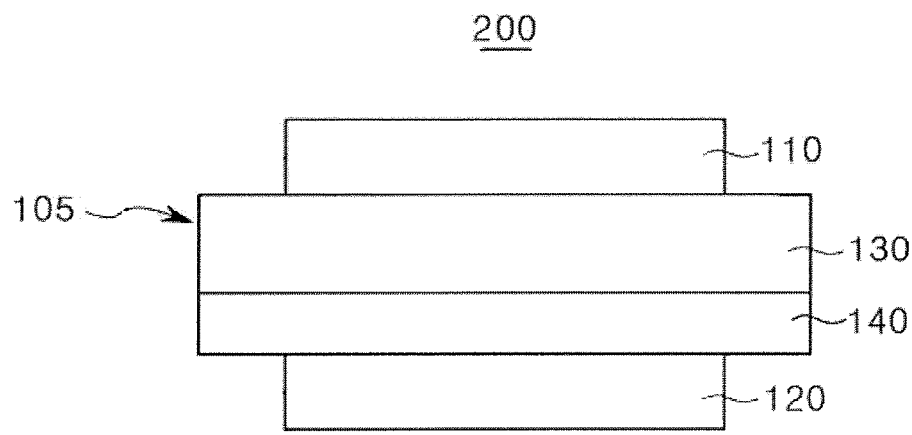

DOPANT FOR ORGANIC OPTOELECTRONIC DEVICE, ORGANIC OPTOELECTRONIC DEVICE AND DISPLAY DEVICE

CROSS REFERENCE TO RELATED APPLICATIONS

This is the U.S. national phase application based on PCT Application No. PCT/KR2015/011322, filed Oct. 26, 2015, which is based on Korean Patent Application No. 10-2015-0063365, filed May 6, 2015, the entire contents of all of which are hereby incorporated by reference.

TECHNICAL FIELD

A dopant for an organic optoelectronic device, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material and has a structure in which an organic layer is disposed between an anode and a cathode.

Performance of the organic light emitting diode may be affected by characteristics of the organic layer and specifically, by characteristics of an organic material in the organic layer. Particularly, a high efficiency light emitting material is required to develop for a large-sized organic light emitting diode, and accordingly, a phosphorescent dopant is being widely used. However, the phosphorescent dopant should inevitably use for example a complex compound including a metal or a heavy metal such as iridium, platinum, copper, beryllium, or the like and costs high.

DISCLOSURE

Technical Problem

According to an embodiment, a dopant for an organic optoelectronic device capable of replacing a complex compound including a metal or a heavy metal and having high wavelength selectivity and efficiency is provided.

An organic optoelectronic device including the dopant is provided.

According to another embodiment, a display device including the organic optoelectronic device is provided.

Technical Solution

According to an embodiment, a dopant for an organic optoelectronic device represented by Chemical Formula 1 is provided.

[Chemical Formula 1]

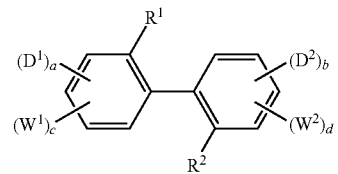

In Chemical Formula 1, $W^1$ and $W^2$ are independently a cyano group; a nitro group; an amide group; a sulfonyl group; a phosphine group; a phosphoryl group: a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; or a combination thereof, $D^1$ and $D^2$ are independently a group represented by Chemical Formula 2, $R^1$ and $R^2$ are independently a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; a combination thereof; or a group represented by Chemical Formula 2, and a, b, c, and d are integers satisfying $0 \le a+b \le 4$ and $0 \le c+d \le 2$, provided that a+b and c+d are not 0 simultaneously,

[Chemical Formula 2]

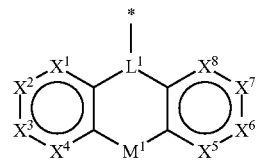

In Chemical Formula 2, $X^1$ to $X^8$ are independently N or $CR^a$, $L^1$ is N, B, C, $CR^b$, or $SiR^c$, $M^1$ is a single bond, $CR^dR^e$, $SiR^fR^g$, $NR^h$, O, or S, $R^a$ is hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group, or a substituted or unsubstituted C3 to C30 heterocyclic group, $R^b$ to $R^h$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, and

* is a linking point with Chemical Formula 1.

According to another embodiment, an organic optoelectronic device includes an anode and a cathode facing each other and an organic layer disposed between the anode and the cathode, wherein the organic layer includes the dopant.

According to another embodiment, a display device including the organic optoelectronic device is provided.

Advantageous Effects

A dopant for an organic optoelectronic device capable of substituting a complex compound including a metal or a heavy metal and having high wavelength selectivity and efficiency is provided.

DESCRIPTION OF DRAWINGS

FIG. 1 is a cross-sectional view showing an organic light emitting diode according to an embodiment, and FIG. 2 is a cross-sectional view showing an organic light emitting diode according to another embodiment.

BEST MODE

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 aryl group, a C2 to C30 heterocyclic group, a C1 to C20 alkoxy group, a C1 to C10 trifluoroalkyl group such as a trifluoromethyl group, or a cyano group.

In addition, two adjacent substituents of the substituted halogen, a hydroxy group, an amino group. C1 to C20 amine group, a nitro group, C3 to C40 silyl group, C1 to C30 alkyl group, C1 to C10 alkylsilyl group. C6 to C30 aryl group. C3 to C30 heterocyclic group, C1 to C20 alkoxy group, C1 to C10 trifluoroalkyl group such as trifluoromethyl group, or cyano group may be fused to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one heteroatom and remaining carbons in one functional group. The heteroatom may be selected from N, O, S, P, and Si.

In the present specification, "an aryl group" refers to a group including at least one hydrocarbon aromatic moiety, and includes hydrocarbon aromatic moieties linked by a single bond and hydrocarbon aromatic moieties fused directly or indirectly to provide a non-aromatic fused ring. The aryl group may include a monocyclic, polycyclic or fused polycyclic (i.e., rings sharing adjacent pairs of carbon atoms) functional group.

In the present specification, "a heterocyclic group" is a concept including a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

More specifically, the substituted or unsubstituted aryl group and/or the substituted or unsubstituted heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted terphenyl group, a substituted or unsubstituted quaterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, a pyridoindolyl group, a benzopyridooxazinyl group, a benzopyridothiazinyl group, a 9,9-dimethyl9,10dihydroacridinyl group, a combination thereof, or a combined fused ring of the foregoing groups, but are not limited thereto. In one example of the present invention, the heterocyclic group or the heteroaryl group may be a pyridyl group, a carbazolyl group, or a pyridoindolyl group.

In the present specification, the substituted or unsubstituted arylene group or the substituted or unsubstituted heteroarylene group or the substituted or unsubstituted divalent heterocyclic group has two linking groups in the substituted or unsubstituted aryl group or the substituted or unsubstituted heterocyclic group, and may be, for example, a substituted or unsubstituted phenylene group, a substituted or unsubstituted naphthalene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quarterphenylene group, a substituted or unsubstituted chrysenylene group, a substituted or unsubstituted triperylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyrrolylene group, a substituted or unsubstituted pyrazolene group, a substituted or unsubstituted imidazolylene group, a substituted or unsubstituted triazolylene group, a substituted or unsubstituted oxazolylene group, a substituted or unsubstituted thiazolylene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolene group, a combination thereof, or a fused form of combinations thereof, but are not limited thereto.

In one example of the present invention, the substituted or unsubstituted arylene group or the substituted or unsubstituted heteroarylene group or the substituted or unsubstituted divalent heterocyclic group may be one of a substituted or unsubstituted phenylene group, a substituted or unsubstituted biphenylene group, a substituted or unsubstituted terphenylene group, a substituted or unsubstituted quaterphenylene group, a substituted or unsubstituted naphthalene group, and a substituted or unsubstituted pyrimidylene group, or a combination thereof.

In the specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

In the present specification, a dopant is a material emitting light in a specific wavelength region by being doped in a host and receiving energy or carrier from a host and is different from a host that is an energy or carrier source.

Hereinafter, a dopant for an organic optoelectronic device according to an embodiment is described.

A dopant for an organic optoelectronic device according to an embodiment is represented by Chemical Formula 1.

[Chemical Formula 1]

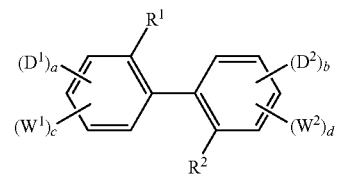

In Chemical Formula 1, $W^1$ and $W^2$ are independently an electron withdrawing group), for example a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; or a combination thereof, $D^1$ and $D^2$ are an electron donating group and independently a group represented by Chemical Formula 2, $R^1$ and $R^2$ are an electron withdrawing group or an electron donating group and are independently a cyano group; a nitro group: an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; a combination thereof; or a group represented by Chemical Formula 2, and a, b, c, and d are integers satisfying $0 \le a+b \le 4$ and $0 \le c+d \le 2$, provided that a+b and c+d are not 0 simultaneously,

[Chemical Formula 2]

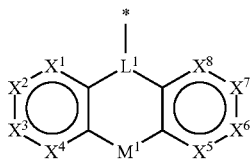

In Chemical Formula 2, $X^1$ to $X^8$ are independently N or $CR^a$, $L^1$ is N, B, C, $CR^b$, or $SiR^c$, $M^1$ is a single bond, $CR^dR^e$, $SiR^fR^g$, $NR^h$, O, or S, $R^a$ is hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group or a substituted or unsubstituted C3 to C30 heterocyclic group.

$R^b$ to $R^h$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, and

* is a linking point with Chemical Formula 1.

For example, $W^1$ and $W^2$ in Chemical Formula 1, may independently be for example an electron withdrawing group, for example a cyano group; a nitro group; an amide group; a halogen; or a C1 to C5 alkyl group substituted a cyano group, a nitro group, or a halogen, $D^1$ and $D^2$ may be an electron donating group and may independently be a group represented by Chemical Formula 2, $R^1$ and $R^2$ may be an electron withdrawing group or an electron donating group, and may independently be a cyano group; a nitro group; a halogen; a C1 to C5 alkyl group substituted with a cyano group, a nitro group, or a halogen; or a group represented by Chemical Formula 2, a, b, c, and d may be integers satisfying $0 \le a+b \le 4$ and $0 \le c+d \le 2$, provided that a+b and c+d are not 0 simultaneously, in Chemical Formula 2, $X^1$ to $X^8$ may independently be N or $CR^a$, $L^1$ may be N, $M^1$ may be a single bond, $CR^dR^e$, $SiR^fR^g$, $NR^h$, O, or S, $R^a$ may be hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group, or a substituted or unsubstituted C3 to C30 heterocyclic group, and $R^b$ to $R^h$ may independently be hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof.

Since the dopant represented by Chemical Formula 1 has a structure that a biphenyl core is substituted with electron donating and withdrawing groups, thereby HOMO-LUMO may be easily separated, and an energy gap between singlet energy and triplet energy may be effectively reduced. Accordingly, since a reverse intersystem crossing (RIC) from the triplet exited state (T1) to the singlet exited state (S1) easily occurs, the dopant may all use fluorescence occurring through the reverse intersystem crossing (RIC) from the triplet exited state (T1) to the singlet exited state (S1) as well as fluorescence of the singlet exited state (S1) and thus increase luminous efficiency.

Furthermore, the dopant represented by Chemical Formula 1 may appropriately cause steric hindrance and thus adjust a distortion among molecules into an appropriate level by introducing substituents $R^1$ and $R^2$ at 2-positions of two phenyl groups of the biphenyl core and appropriately controlling the number of the electron donating groups ($D^1$ and $D^2$) and the electron withdrawing groups ($W^1$ and $W^2$) and accordingly, effectively reduce a full width at half maximum (FWHM). Herein, the full width at half maximum (FWHM) is a width of a wavelength region corresponding to a half of maximum light-emitting, and when the full width at half maximum (FWHM) is narrow, the dopant may selectively emit light in a narrow wavelength region and thus accomplish high wavelength selectivity and high color purity.

For example, two phenyl groups in the biphenyl core of Chemical Formula 1 may be distorted to have an angle of about 30 degrees to 70 degrees.

For example, the dopant represented by Chemical Formula 1 may be a fluorescent dopant having a maximum light-emitting wavelength ($\lambda_{max}$) in about 380 nm to 580 nm.

For example, the dopant represented by Chemical Formula 1 may have an energy bandgap of about 2.5 eV to 3.5 eV.

For example, the dopant represented by Chemical Formula 1 may have an energy gap ($|S^1-T^1|$) between the singlet energy and the triplet energy of less than or equal to about 0.2 eV. For example, the dopant represented by Chemical Formula 1 may have an energy gap ($|S^1-T^1|$) between the singlet energy and the triplet energy in a range of about 0.01 to 0.20 eV.

For example, the dopant represented by Chemical Formula 1 may show a light-emitting spectrum having a full width at half maximum (FWHM) of less than or equal to about 100 nm and specifically, of less than or equal to about 80 nm within the range in a thin film state. Herein, the thin film state may be obtained through radiation of an ultraviolet-visible ray (UV-Vis) into the thin film with a Cary 5000 UV spectroscope (Varian Medical System) in a 50 nm to 100 nm-thick thin film manufactured through thermal evaporation under high vacuum (<$10^{-7}$ Torr) at a speed of 0.5 to 1.0 Å/s. In addition, the thin film state may be obtained by co-depositing a host and a dopant or dispersing them in polystyrene.

For example, the dopant represented by Chemical Formula 1 may show a light-emitting spectrum having a full width at half maximum (FWHM) ranging from about 30 nm to 100 nm and for example, from about 30 nm to 80 nm within the range in the thin film state.

Accordingly, the dopant represented by Chemical Formula 1 may be used as a fluorescent dopant having high efficiency and high color purity and replacing a conventional phosphorescent dopant including a heavy metal such as iridium, platinum, copper, or the like.

In Chemical Formula 1, the substituents ($R^1$ and $R^2$) at the 2-positions of two phenyls of the biphenyl core may be independently the electron donating group or the electron withdrawing group, for example, $R^1$ may be the same as $W^1$ or $D^1$, and $R^2$ may be the same as $W^2$ or $D^2$ in Chemical Formula 1.

The dopant represented by Chemical Formula 1 may be for example represented by one of Chemical Formulae 1-I to 1-IV.

[Chemical Formula 1-I]

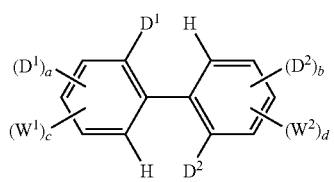

[Chemical Formula 1-II]

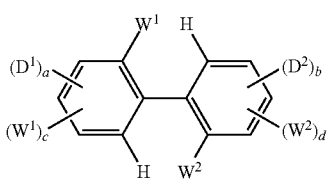

[Chemical Formula 1-III]

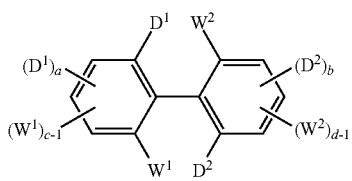

[Chemical Formula 1-IV]

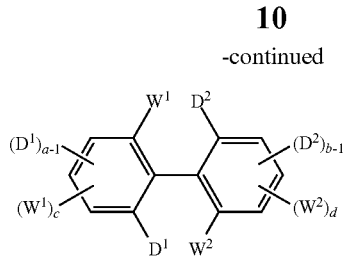

In Chemical Formulae 1-I to 1-IV, $W^1$, $W^2$, $D^1$, $D^2$, a, b, c, and d are the same as described above.

In Chemical Formula 1-III or 1-IV, a-1 is one smaller integer than a, b-1 is one smaller integer than b, c-1 is one smaller integer than c, and d-1 is one smaller integer than d.

For example, in Chemical Formulae 1-I to 1-IV, the total number of $D^1$ and $D^2$ may be to 5 and the total number of $W^1$ and $W^2$ may be 1 to 3. For example, the total number of $D^1$ and $D^2$ may be 4 and the total number of $W^1$ and $W^2$ may be 2.

For example, in Chemical Formulae 1-I to 1-IV, $D^1$ and $W^1$ may be linked in an ortho position and $D^2$ and $W^2$ may be linked in an ortho position.

For example, in Chemical Formulae 1-I to 1-IV, two $D^1$'s may be linked in an ortho position and two $D^2$'s may be linked in an ortho position.

For example, in Chemical Formulae 1 and 1-I to 1-IV, $W^1$ and $W^2$ may independently be a cyano group; a halogen; a C1 to C10 alkyl group substituted with a cyano group or a halogen; a C6 to C30 aryl group substituted with a cyano group or a halogen; or a C3 to C30 heterocyclic group substituted with a cyano group or a halogen. The halogen may be for example fluorine.

For example, in Chemical Formulae 1, and 1-I to 1-IV, $W^1$ and $W^2$ may independently be a cyano group, a halogen, a methyl group substituted with a cyano group, a methyl group substituted with a halogen, a phenyl group substituted with a cyano group, a biphenyl group substituted with a cyano group, a naphthyl group substituted with a cyano group, a phenyl group substituted with a halogen, a biphenyl group substituted with a halogen, a naphthyl group substituted with a halogen, but are not limited thereto. In addition, for example, in Chemical Formulae 1 and 1-I to 1-IV, $W^1$ and $W^2$ may independently be selected from a cyano group, and a methyl group substituted with a halogen or a cyano group.

For example, in Chemical Formulae 1 and 1-I to 1-IV, $D^1$ and $D^2$ may be independently represented by one of Chemical Formulae 2-I to 2-VI.

[Chemical Formula 2-I]

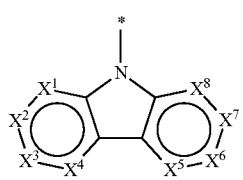

[Chemical Formula 2-II]

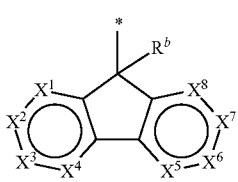

[Chemical Formula 2-III]

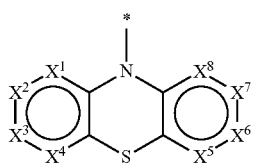

[Chemical Formula 2-IV]

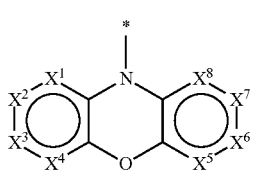

[Chemical Formula 2-V]

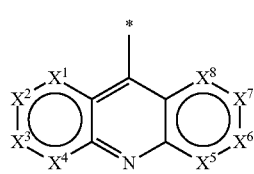

[Chemical Formula 2-VI]

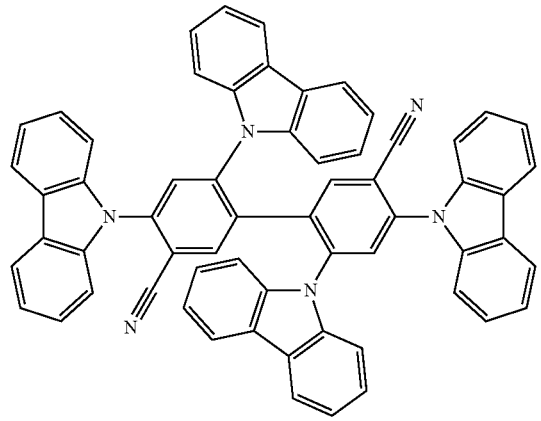

In Chemical Formulae 2-I to 2-VI, $X^1$ to $X^8$, $R^a$, $R^b$, $R^d$, and $R^e$ are the same as described above. For example, Chemical Formula 2 of the present invention may be Chemical Formula 2-1.

For example, in Chemical Formulae 2 and 2-I to 2-VI, $X^1$ to $X^8$ may be $CR^a$, wherein $R^a$'s may be independently the same or different and are the same as described above.

For example, in Chemical Formulae 2 and 2-I to 2-VI, one, two, or three of $X^1$ to $X^8$ may be N and the remainder may be $CR^a$. Herein $R^a$'s may be independently the same or different and are the same as described above. In Chemical Formulae 2, and 2-I to 2-VI, one of $X^1$ to $X^8$ may be N and the remainder may be CH. In Chemical Formulae 2, 2-I to 2-VI, one of $X^1$ to $X^4$ may be N, one of $X^5$ to $X^8$ may be N, and the remainder may be CH.

The dopant represented by Chemical Formula 1 may be for example one of compounds of Group 1, but is not limited thereto. In Group 1, "Cz" refers to a carbazolyl group.

[Group 1]

1

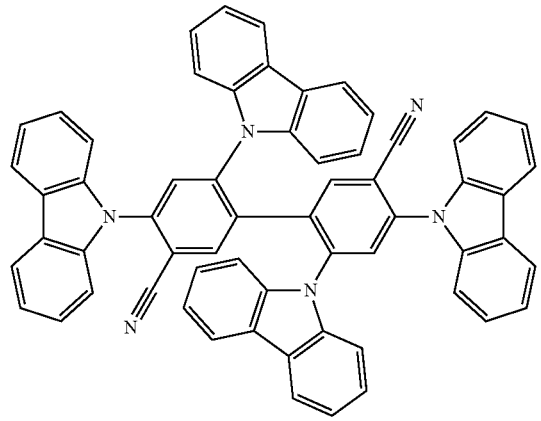

2

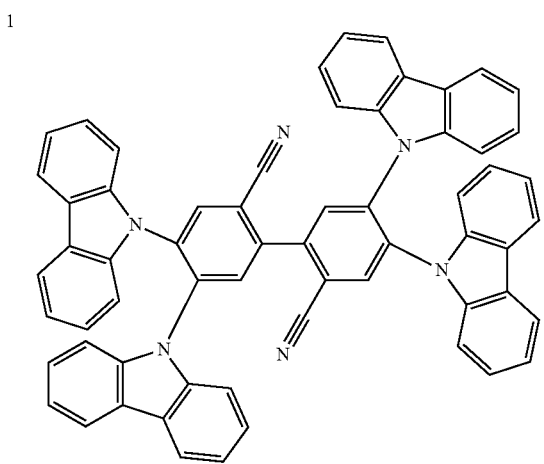

3

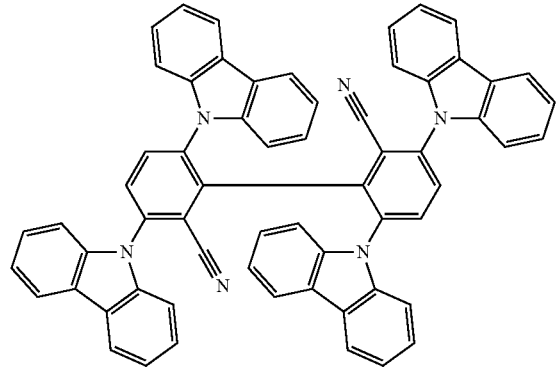

4

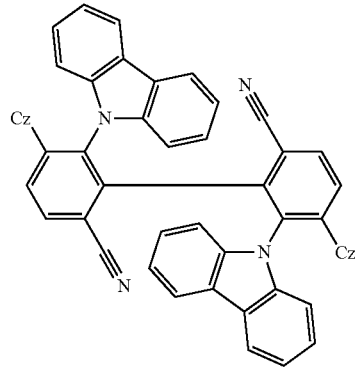

-continued
5
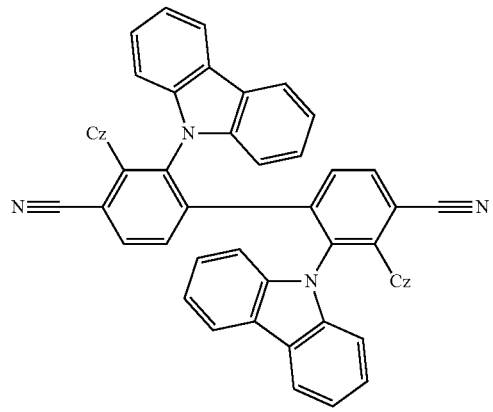
6
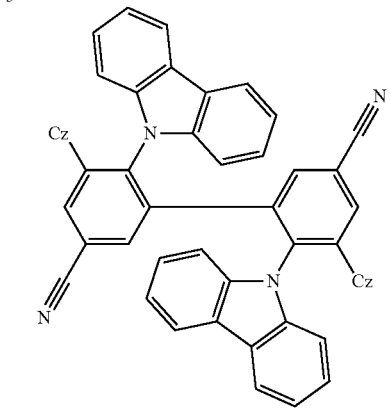
7
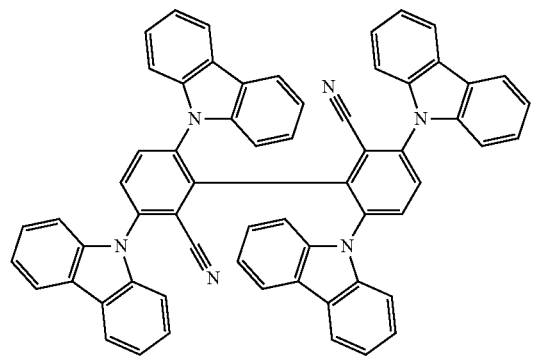
8
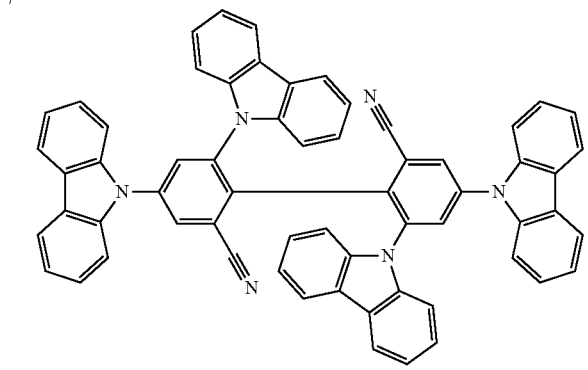
9
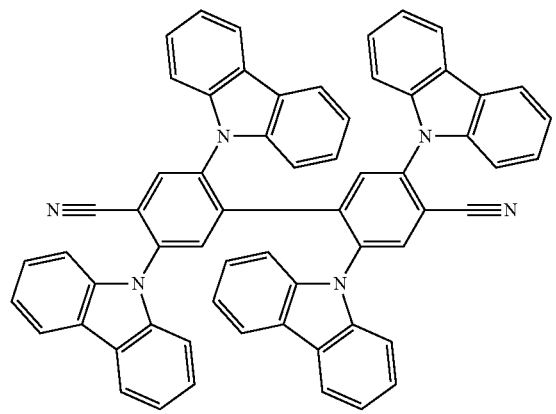
10
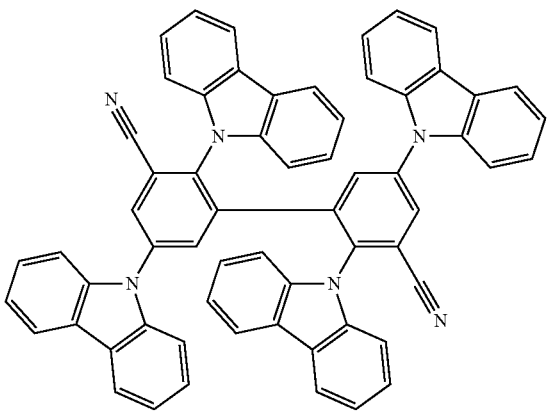
11
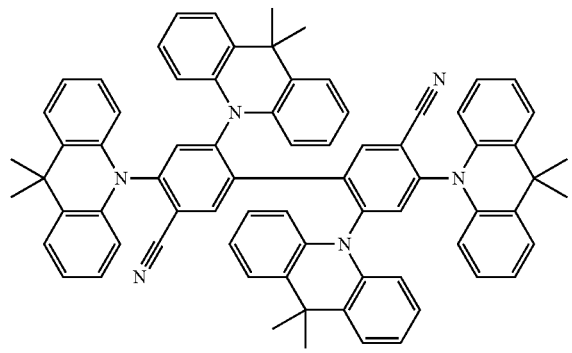
12
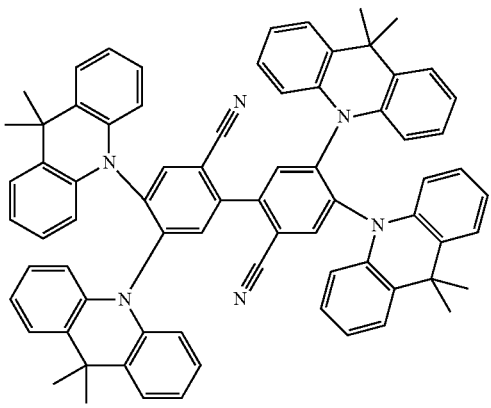

-continued
13
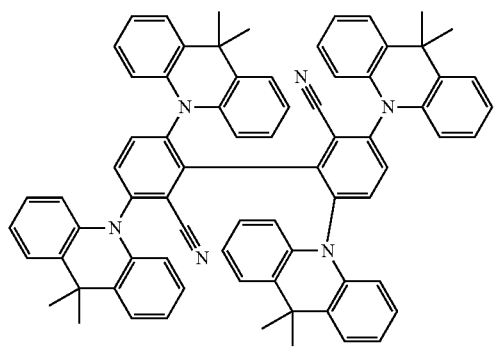
14
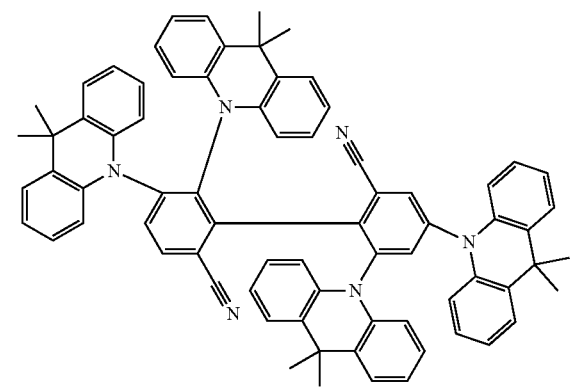
15
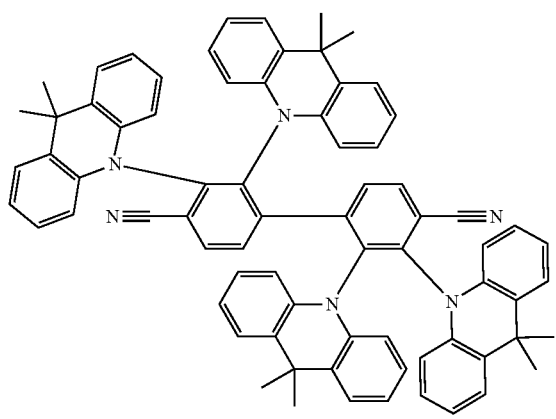
16
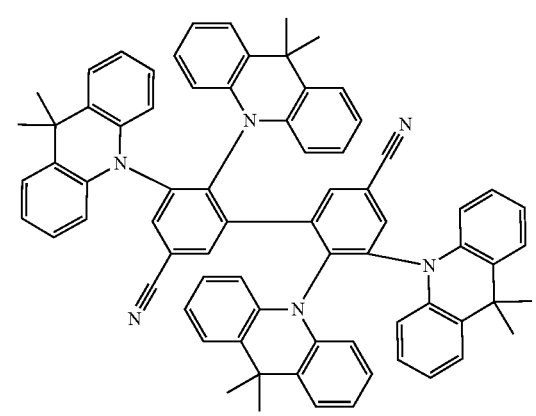
17
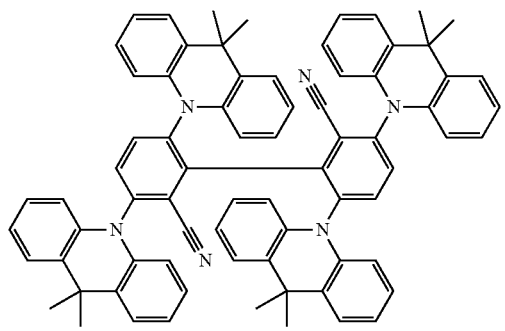
18
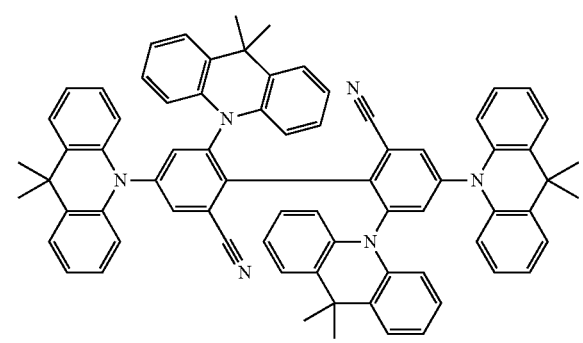
19
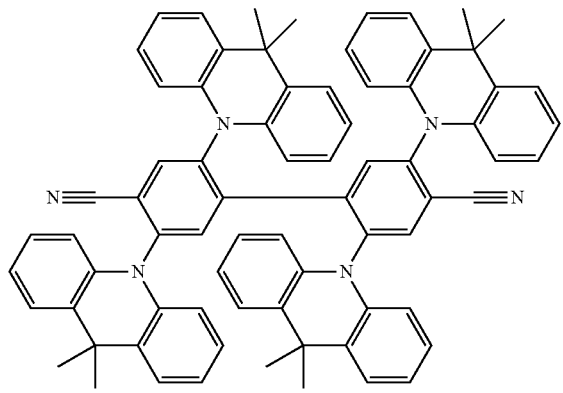
20
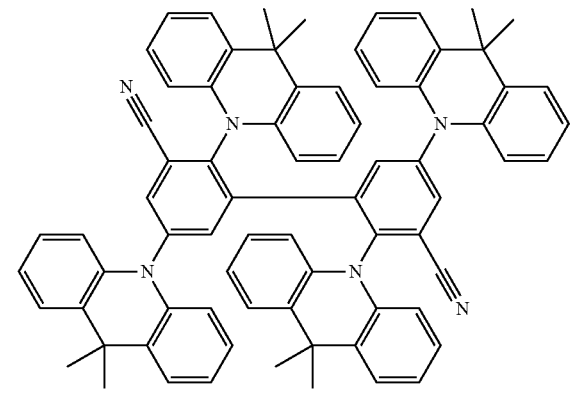

-continued
21
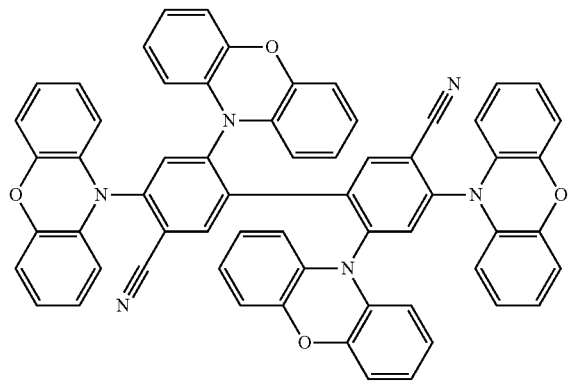
22
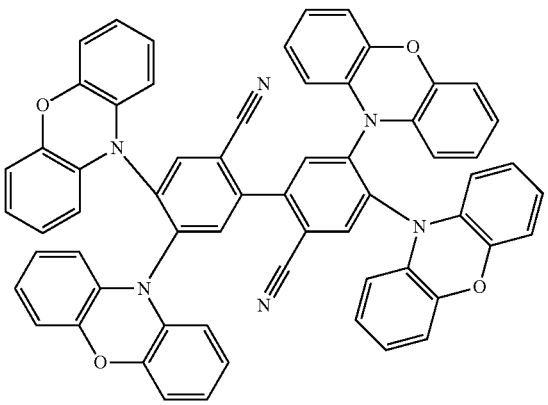
23
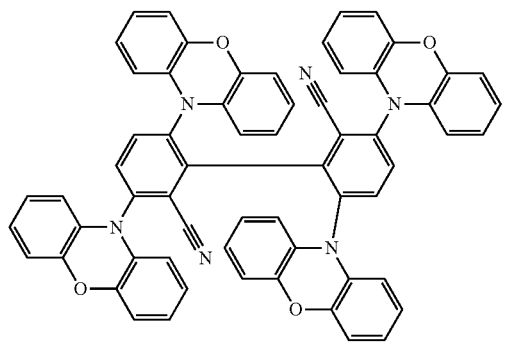
24
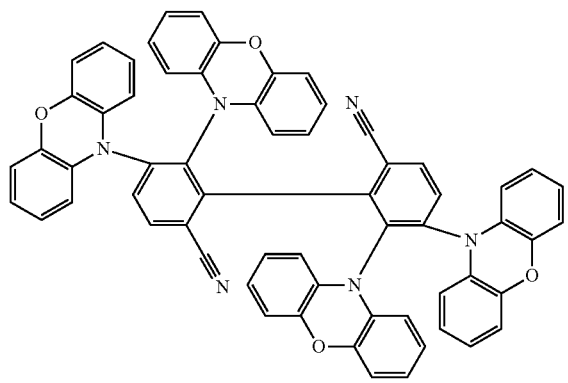
25
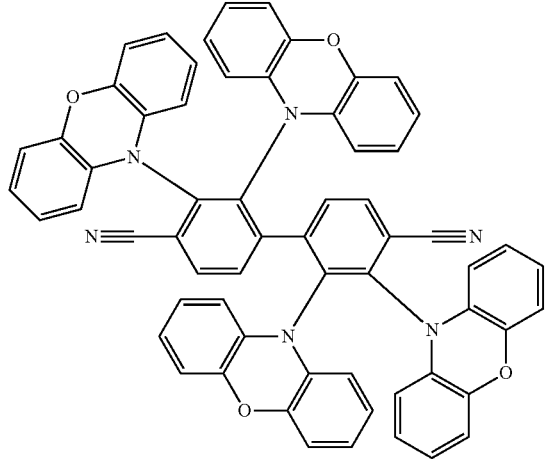
26
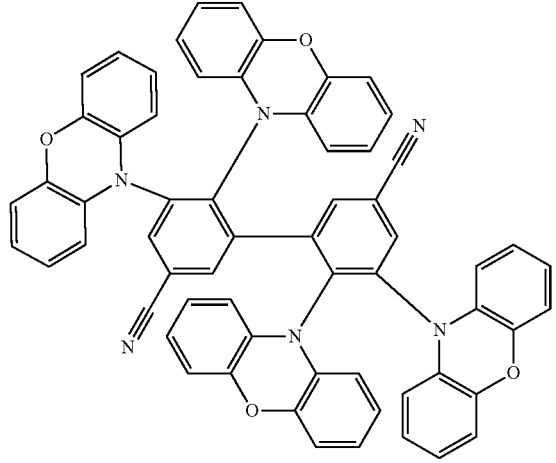
27
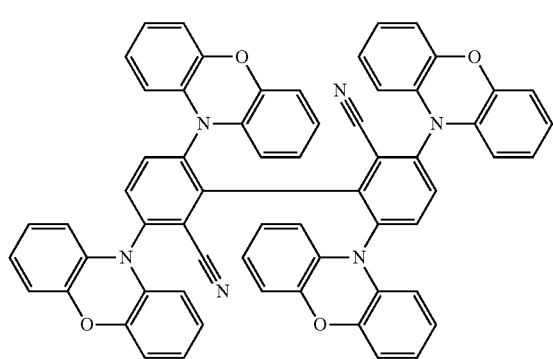
28
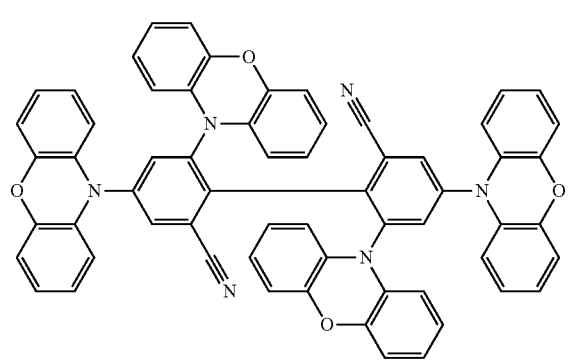

-continued
29
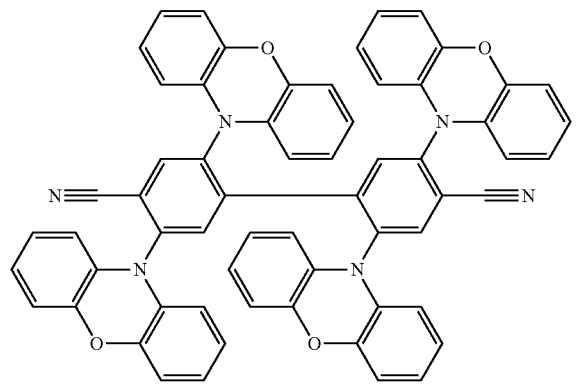
30
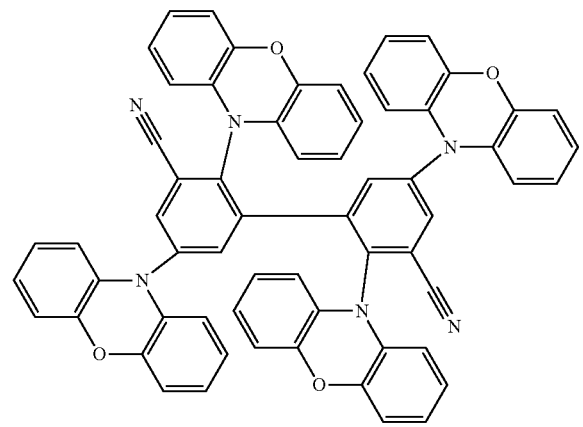
31
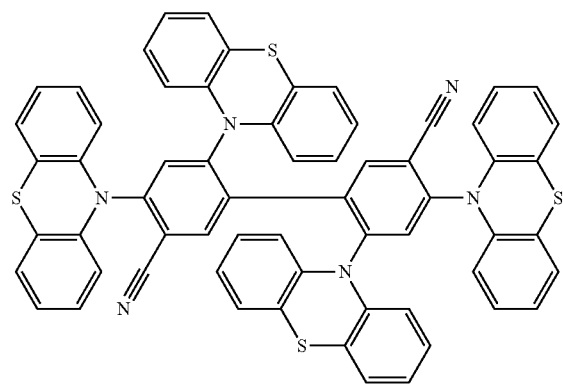
32
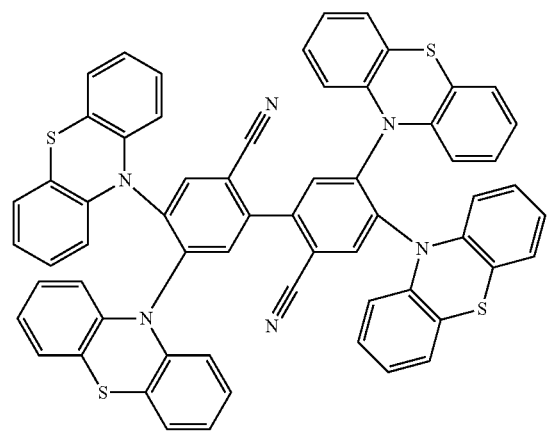
33
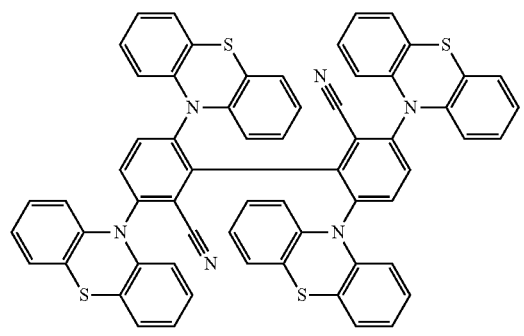
34
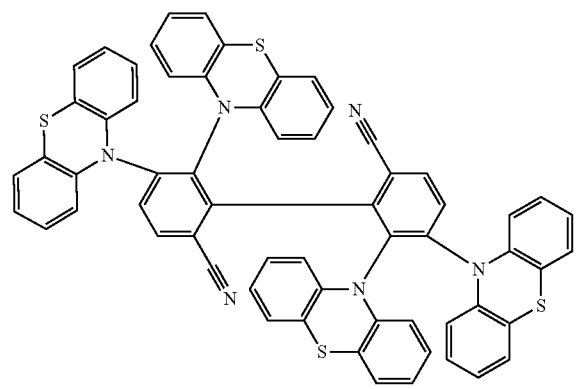

35
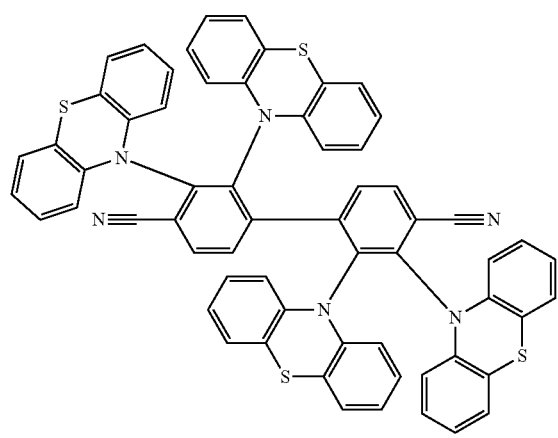
36
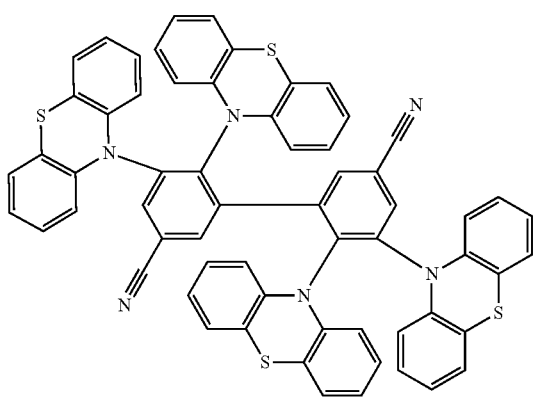
37
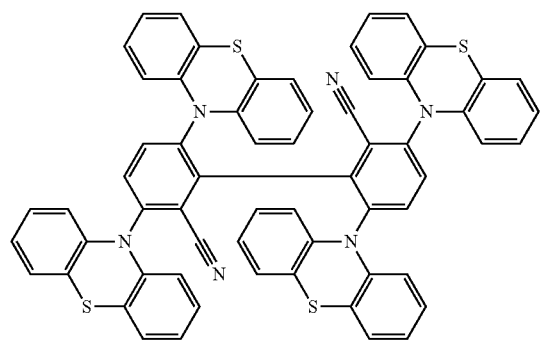
38
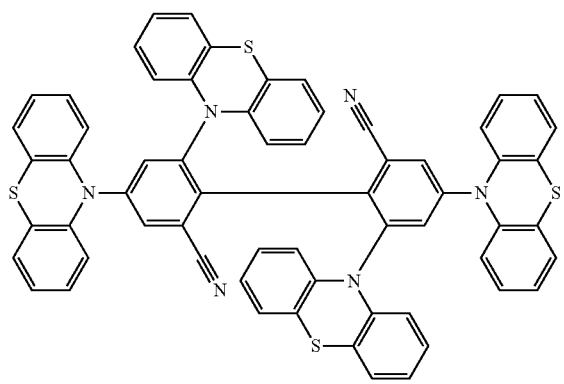
39
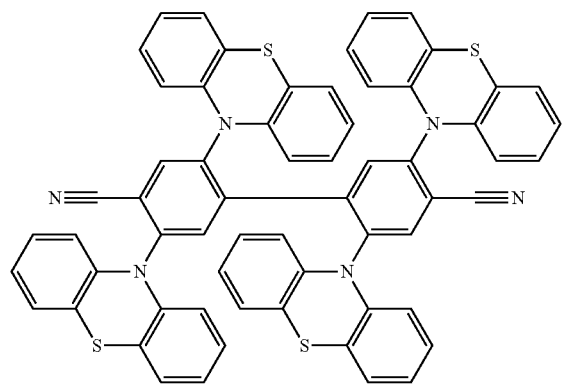
40
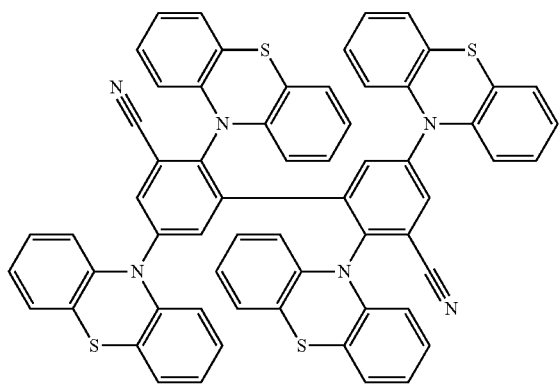

-continued
41
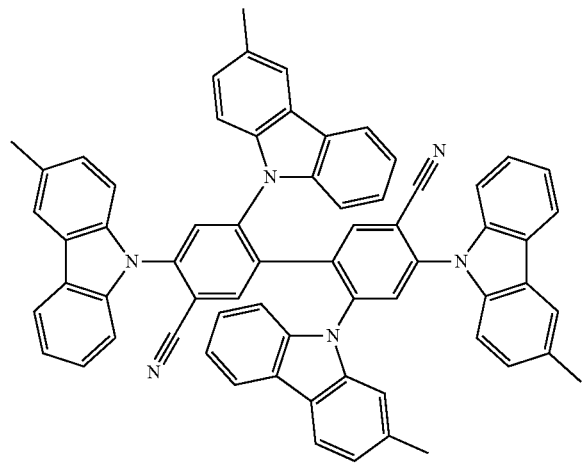
42
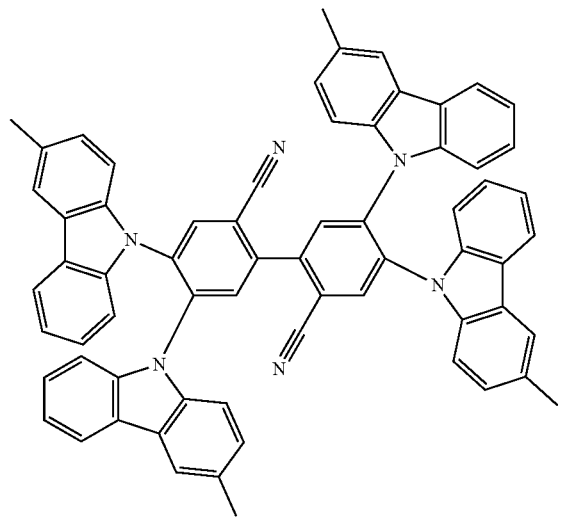
43
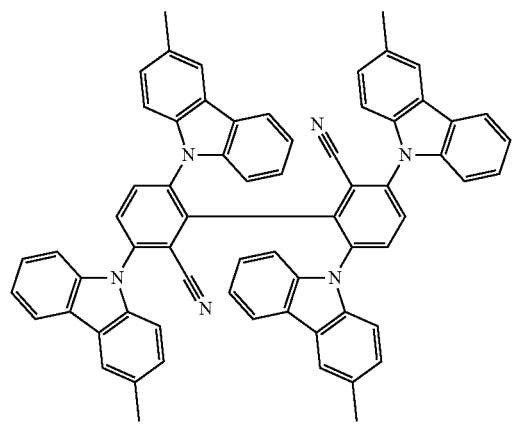
44
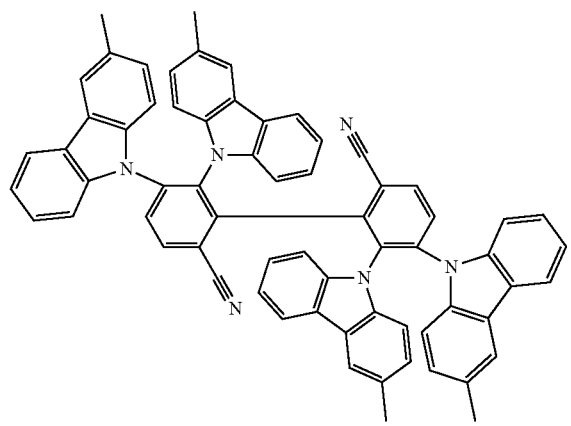
45
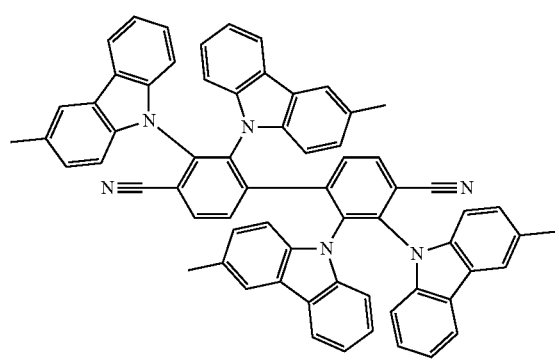
46
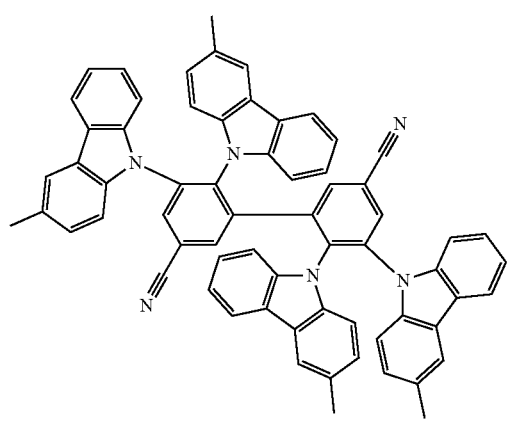

-continued
47
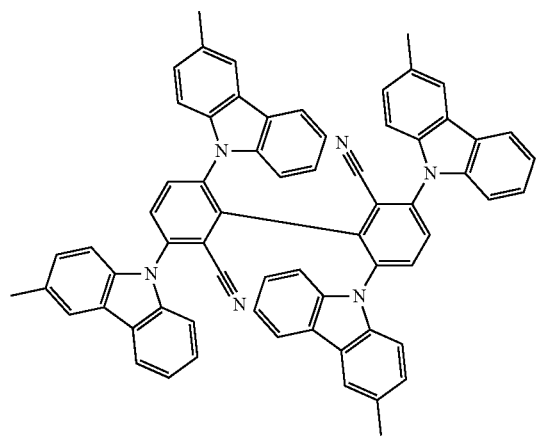
48
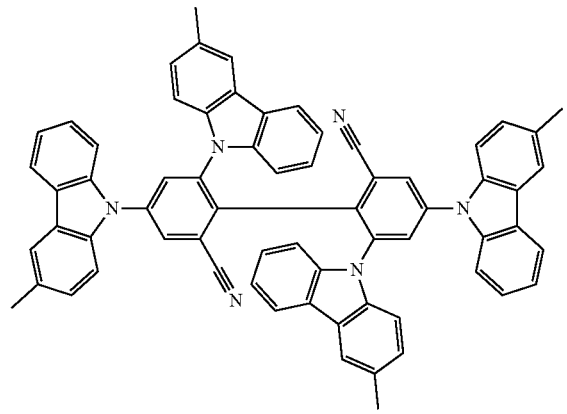
49
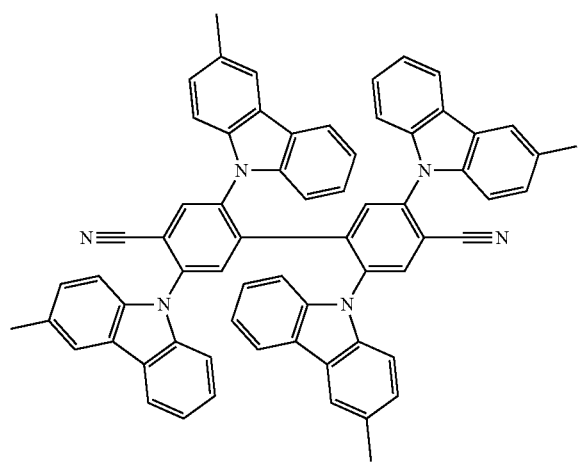
50
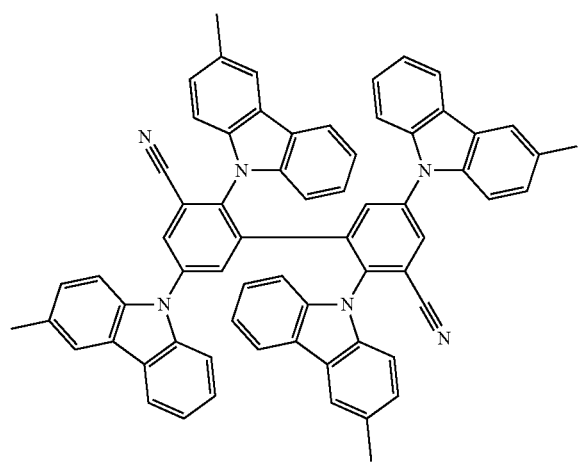
51
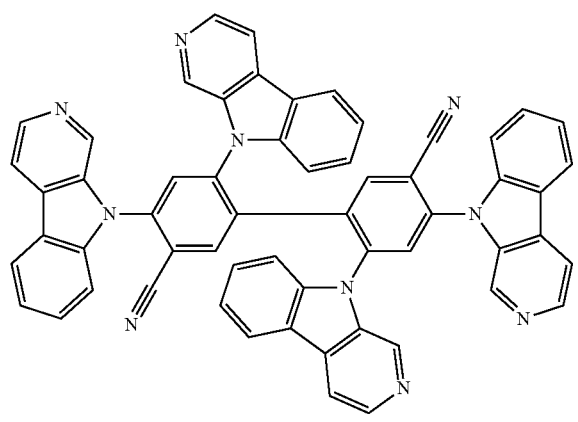
52
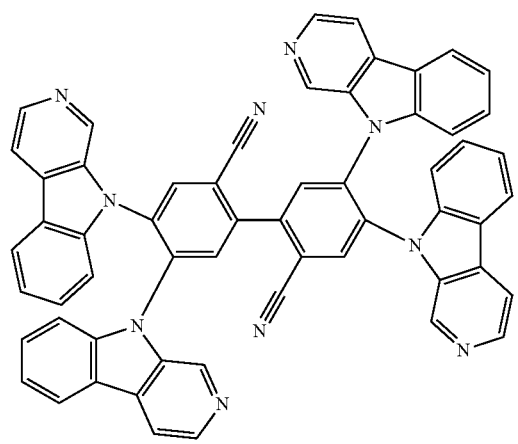

-continued
53
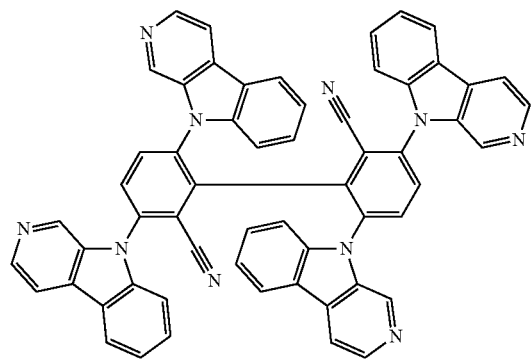
54
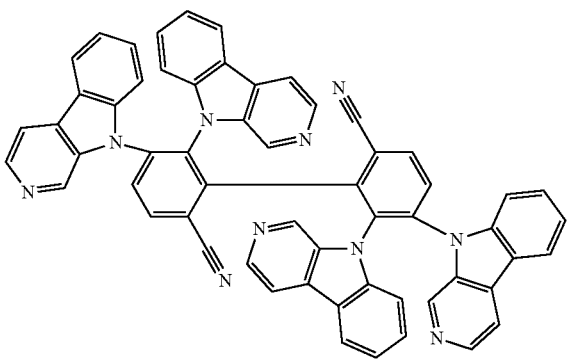
55
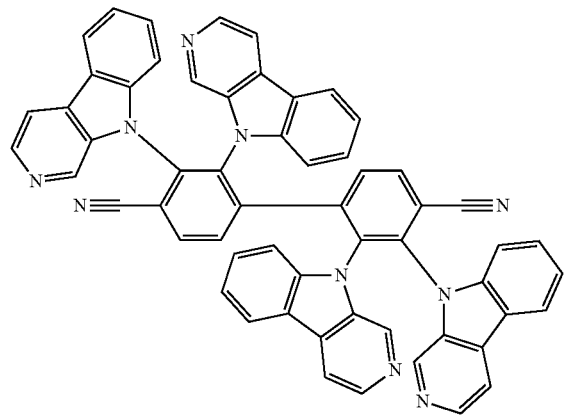
56
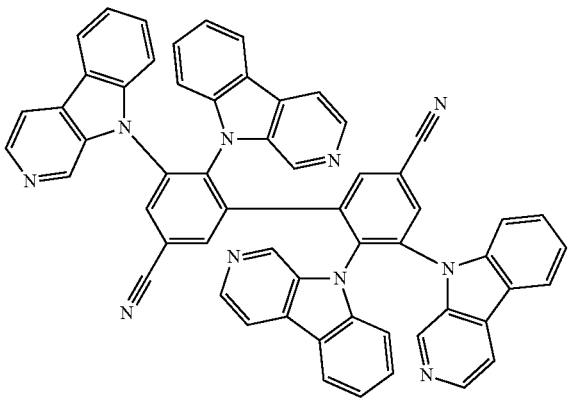
57
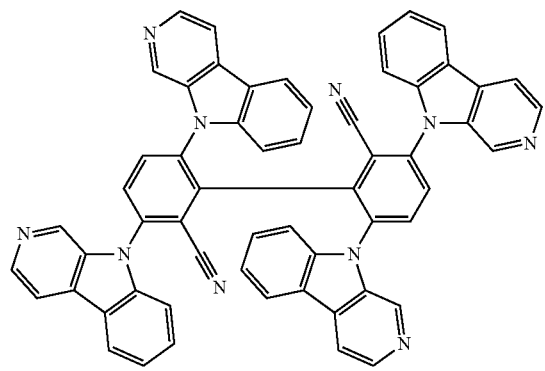
58
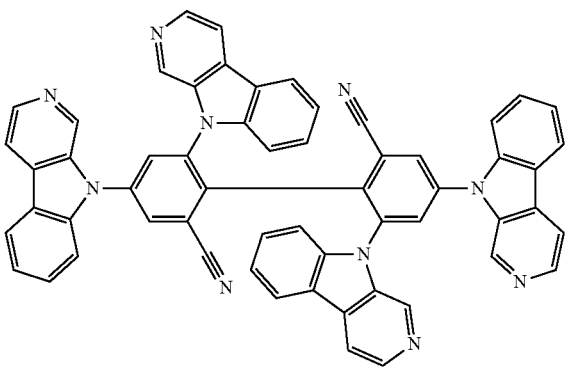
59
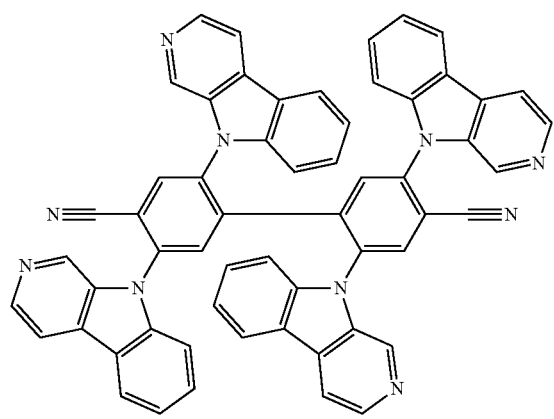
60
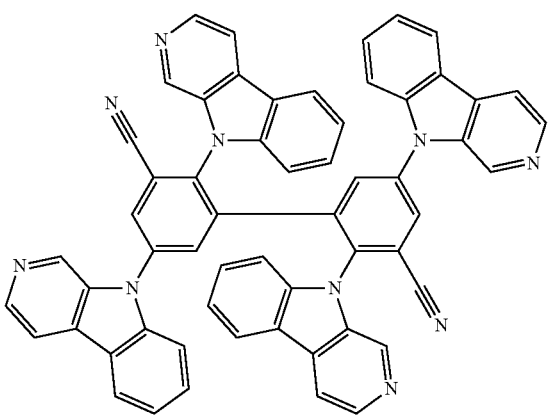

-continued
61
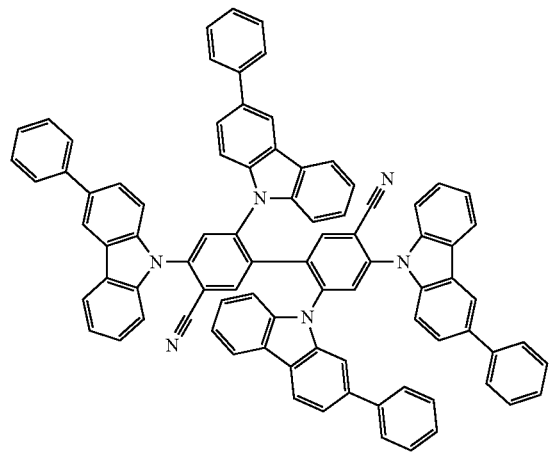
62
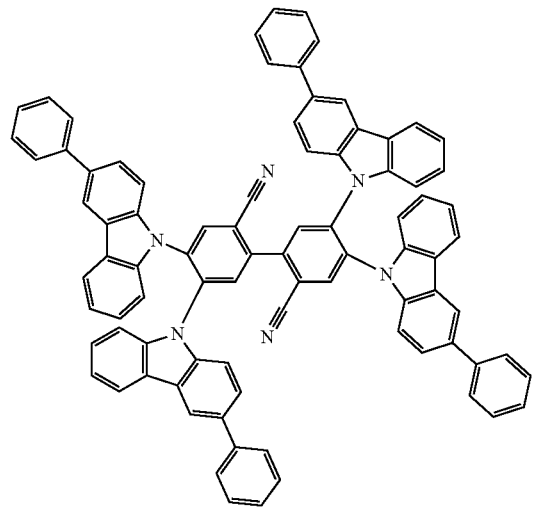
63
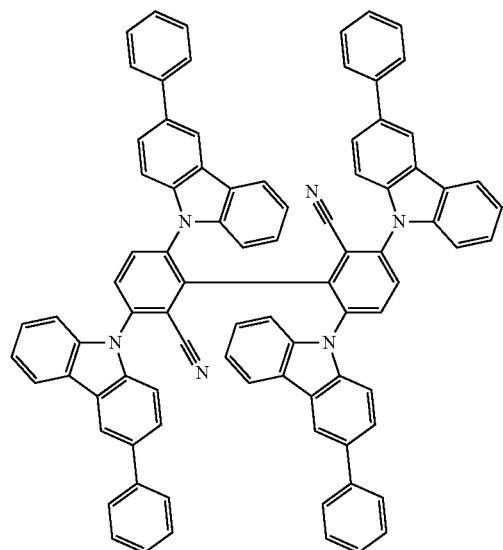
64
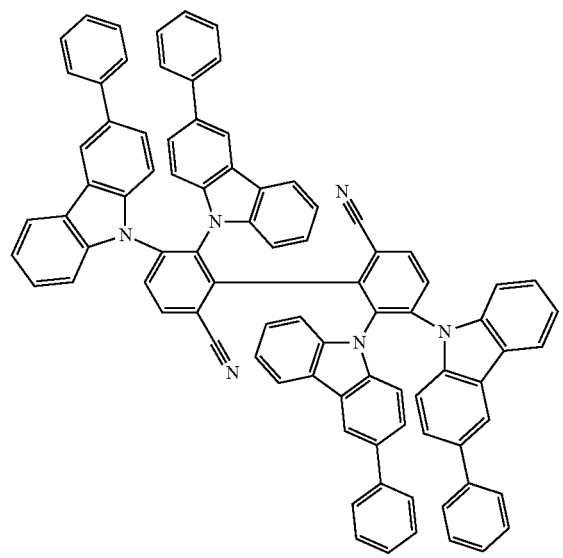
65
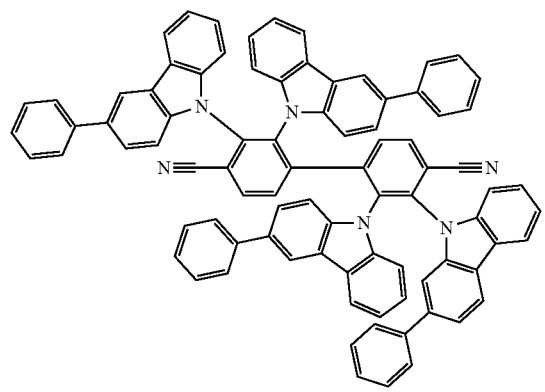
66
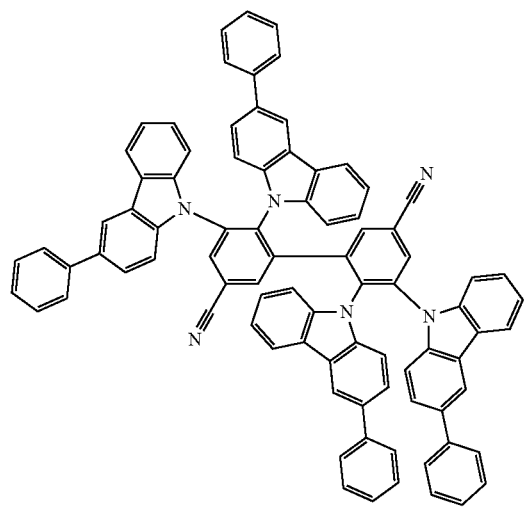

67
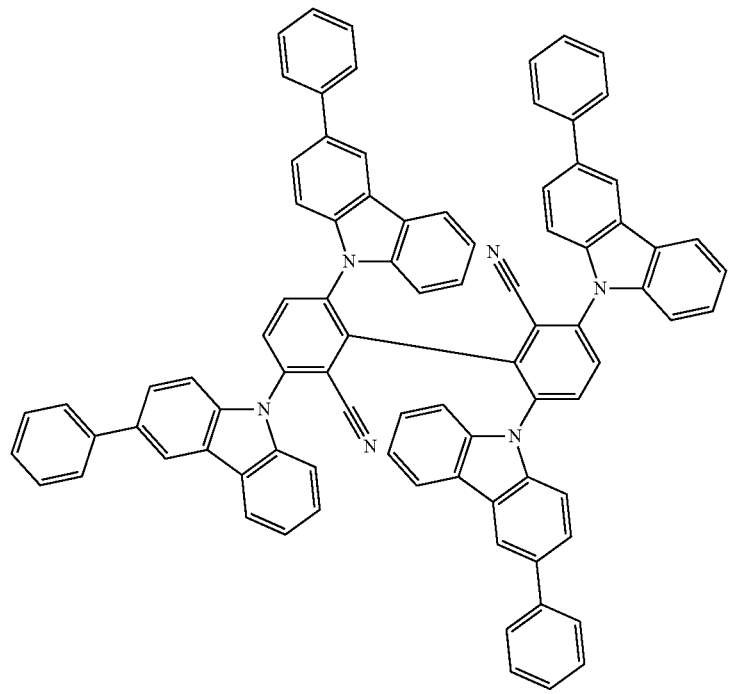
68
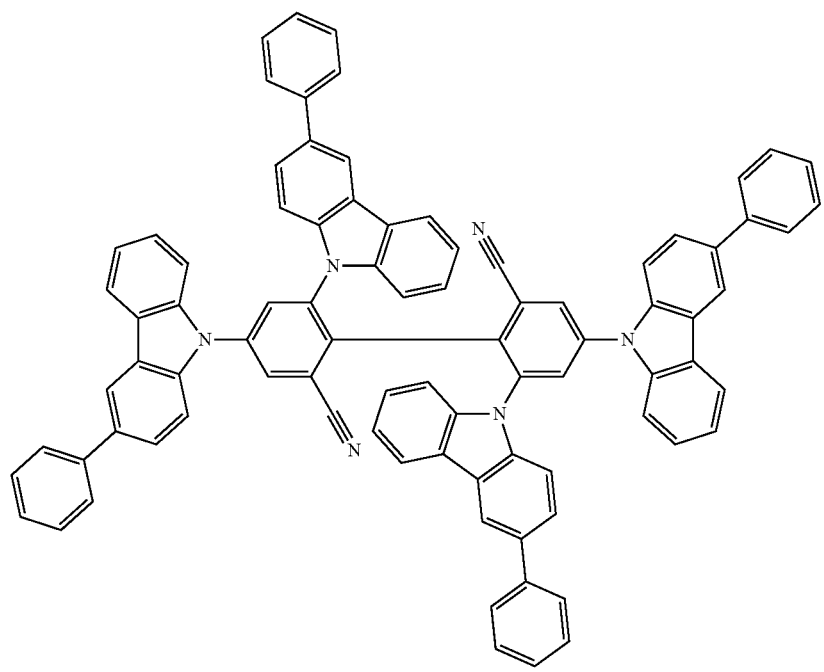

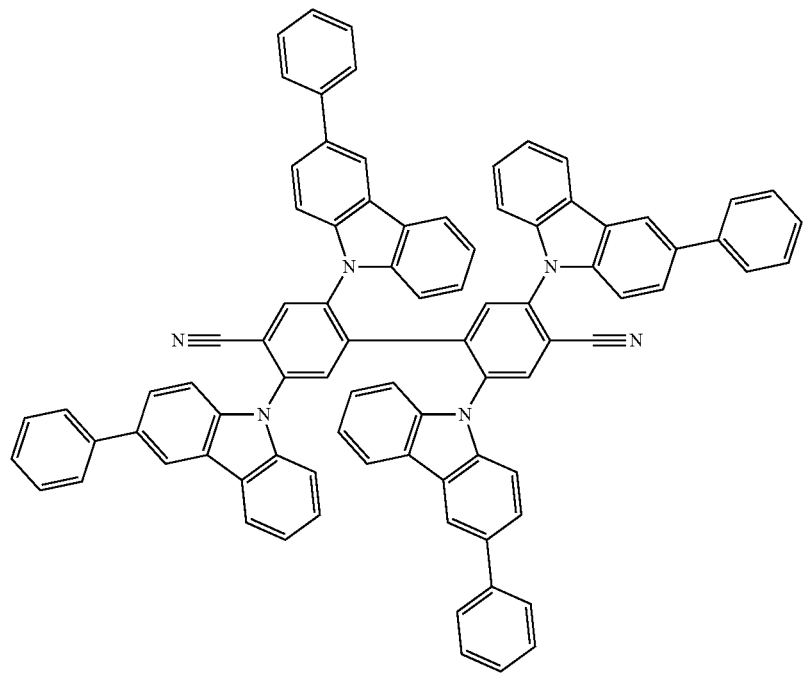

69

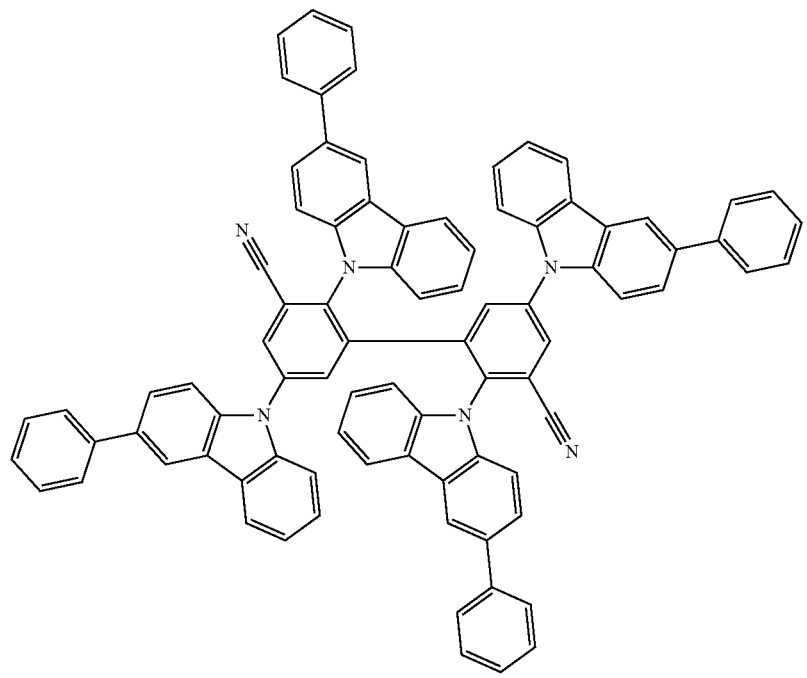

70

Hereinafter, an organic optoelectronic diode including the dopant is described.

The organic optoelectronic device may be any device to convert electrical energy into photoenergy and vice versa without particular limitation, and may be, for example an organic photoelectric device, an organic light emitting diode, an organic solar cell, and an organic photo conductor drum.

The organic optoelectronic device may include an anode and a cathode facing each other, at least one organic layer between the anode and the cathode, and the organic layer may include at least one host and the dopant.

Herein, an organic light emitting diode as one example of an organic optoelectronic device is described referring to drawings.

FIG. 1 is a cross-sectional view showing an organic light emitting diode according to an embodiment.

Referring to FIG. 1, an organic light emitting diode 100 according to an embodiment includes an anode 110 and a cathode 120 and an organic layer 105 between the anode 110 and the cathode 120.

The anode 110 may be made of a conductor having a high work function to help hole injection, and may be for example a metal, a metal oxide and/or a conductive polymer.

The anode 110 may be for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 120 may be made of a conductor having a low work function to help electron injection, and may be for example a metal, a metal oxide and/or a conductive polymer. The cathode 120 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al, and $BaF_2$/Ca, but is not limited thereto.

The organic layer 105 includes a light emitting layer 130 including at least one host and the dopant.

The host may be a single host or a mixed host including two or more. The host may be selected from material having a larger energy bandgap than the dopant.

The dopant is the same as described above and is mixed with a host and receives energy from the host to emit light in a specific wavelength region. As described above, the dopant may be a fluorescent dopant having high efficiency and color purity capable of replacing a phosphorescent dopant including a heavy metal.

The dopant may be for example a fluorescent dopant having a maximum light-emitting wavelength ($\lambda_{max}$) in about 380 nm to about 580 nm.

The dopant may exhibit for example a light-emitting spectrum having a full width at half maximum (FWHM) of less than or equal to about 100 nm in a thin film state, and within the range, a light-emitting spectrum having a full width at half maximum (FWHM) of less than or equal to about 80 nm in a thin film state. For example, the dopant represented by Chemical Formula 1 may exhibit for example a light-emitting spectrum having a full width at half maximum (FWHM) of about 10 nm to about 100 nm in a thin film state, a light-emitting spectrum having a full width at half maximum (FWHM) of about 30 nm to 100 nm in a thin film state, within the range a light-emitting spectrum having a full width at half maximum (FWHM) of about 30 nm to 80 nm in a thin film state.

The dopant may be included in a smaller amount than the host. For example, the dopant may be included in an amount of about 0.01 to 40 wt %, within the range about 0.01 to 30 wt %, and within the range about 0.01 to 20 wt % based on a total amount of the host and the dopant.

The organic layer 105 may be formed using a dry film formation method or a solution process. The dry film formation method may be for example a chemical vapor deposition (CVD) method, sputtering, plasma plating, and ion plating, and two or more compounds may be simultaneously formed into a film or compound having the same deposition temperature may be mixed and formed into a film. The solution process may be for example inkjet printing, spin coating, slit coating, bar coating and/or dip coating.

FIG. 2 is a cross-sectional view showing an organic light emitting diode according to another embodiment.

Referring to FIG. 2, an organic light emitting diode 200 of the present embodiment includes an anode 110 and a cathode 120 and an organic layer 105 disposed between the anode and the cathode 120 like the embodiment.

The organic layer 105 includes a light emitting layer 130 and an auxiliary layer 140 disposed between the light emitting layer 130 and the cathode 120. The auxiliary layer 140 may facilitate injection and transport of charge carriers between the cathode 120 and the light emitting layer 130. The auxiliary layer 140 may be for example an electron transport layer, an electron injection layer, and/or an electron transport auxiliary layer.

In FIGS. 1 and 2, the organic layer 105 may further include at least one auxiliary layer disposed between the anode 110 and the light emitting layer 130.

The organic light emitting diode may be applied to an organic light emitting diode display.

Hereinafter, the embodiments are illustrated in more detail with reference to examples. These examples, however, are not in any sense to be interpreted as limiting the scope of the invention.

Synthesis of Intermediate

Synthesis of Intermediate I-1

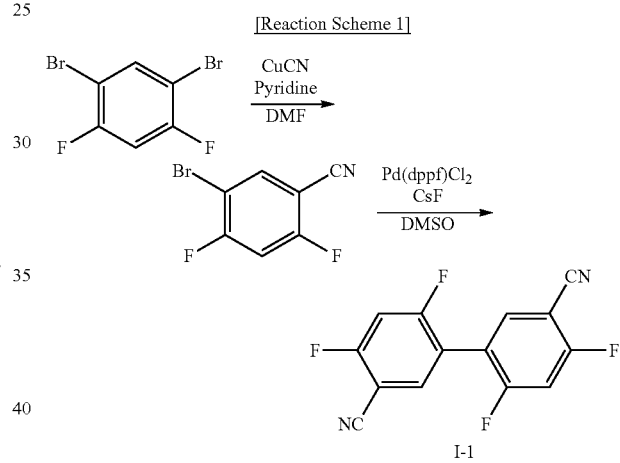

1,5-dibromo-2,4-difluorobenzene (10 g, 36.0 mmol) and CuCN (5.5 g, 60.9 mmol) were dissolved in DMF (30 ml), pyridine (3 ml) was added thereto, and the mixture was bubbled with nitrogen to remove oxygen therein. The reactant was heated up to 120° C., and stirred. Subsequently, the resultant was reacted for about 8 hours and cooled down, distilled water was added thereto to complete the reaction, and ethylether was used for an extraction. The reactant was washed with a 10% ammonia aqueous solution and then, with a concentrated ammonium chloride aqueous solution. Subsequently, the reactant was lastly washed with a concentrated sodium bicarbonate aqueous solution and extracted with ethylether. Then, the reactant was column-purified by using an eluting solvent such as ethylacetate and normal hexane to obtain 3.0 g of 5-bromo-2,4-difluorobenzonitrile. The 5-bromo-2,4-difluorobenzonitrile (3.0 g, 13.8 mmol), Pd(dppf)$Cl_2$ (1.1 g, 1.4 mmol), and cesium fluoride (6.3 g, 41.2 mmol) were dissolved in DMSO (20 ml), and the solution was stirred for 3 hours under a nitrogen atmosphere while maintained at 100° C. The temperature was cooled down, distilled water was added thereto to complete a reaction, and dichloromethane was used for an extraction. A mixed solvent of dichloromethane and normal hexane was used as an eluting solvent to obtain 0.4 g of Intermediate I-1.

Intermediate I-1: mass analysis (FI) m/z 276 [(M+)]. 1H NMR (200 MHz, CDCl3): δ 7.69 (t, 2H), 6.92 (t, 2H).

Synthesis of Intermediate I-2

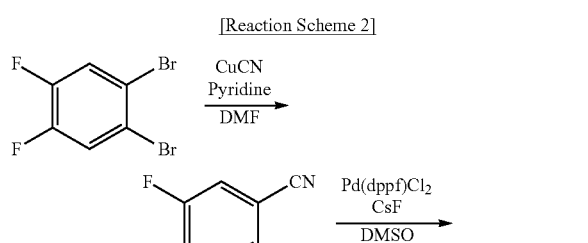

[Reaction Scheme 2]

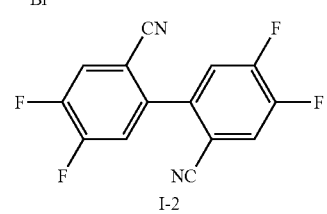

0.3 g of Intermediate I-2 was synthesized according to the same method as the method of synthesizing Intermediate I-1 except for using 1,2-dibromo-4,5-difluorobenzene instead of 1,5-dibromo-2,4-difluorobenzene.

Intermediate I-2: mass analysis (FAB) m/z 276 [(M+)]. 1H NMR (200 MHz, CDCl3): δ 7.71-7.56 (m, 2H), 7.45-7.12 (m, 2H).

Synthesis of Intermediate I-3

[Reaction Scheme 3]

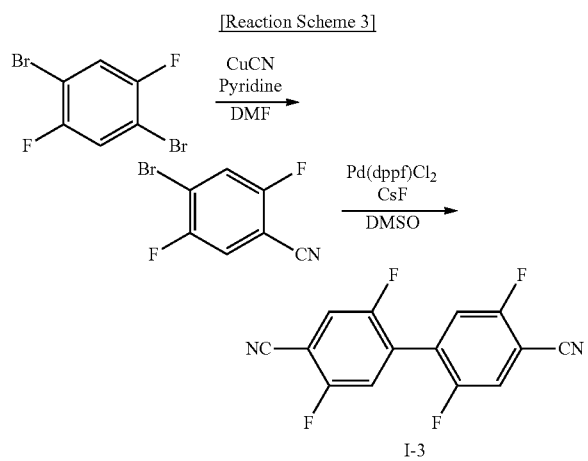

0.2 g of Intermediate I-3 was synthesized according to the same method as the method of synthesizing Intermediate I-1 except for using 1,4-dibromo-2,5-difluorobenzene instead of 1,5-dibromo-2,4-difluorobenzene.

Intermediate I-3: mass analysis (FAB) m/z 276 [(M+)]. 1H NMR (200 MHz, CDCl3): δ 7.77-7.51 (m, 2H), 7.46-7.23 (m, 2H).

Synthesis of Final Compound

Synthesis Example 1: Synthesis of Dopant 1

[Reaction Scheme 4]

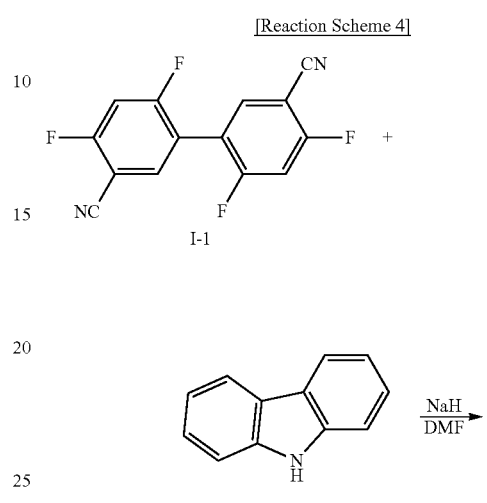

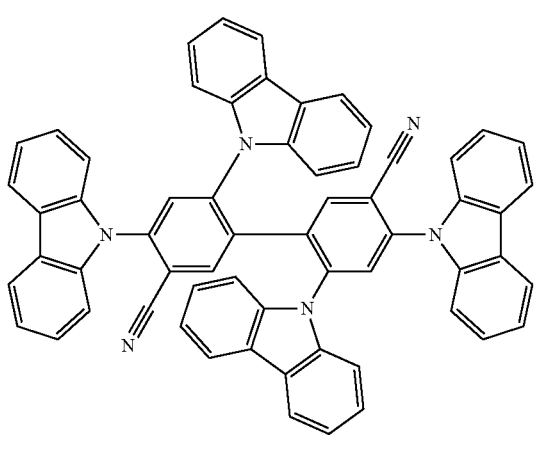

Sodium hydride (0.17 g, 4.3 mmol) was dispersed in DMF (20 ml, 9H-carbazole (0.6 g, 3.6 mmol) was added thereto, the mixture was stirred at room temperature, and when the carbazole and the sodium hydride were all dissolved therein, Intermediate I-1 (0.25 g, 0.7 mmol) was slowly added thereto in a dropwise fashion. The obtained mixture was reacted for 3 hours, distilled water was added thereto to complete the reaction, and dichloromethane was used for an extraction. The resultant was treated through column chromatography by using a mixture of chloroform and normal hexane as an eluting solvent to obtain Dopant 1 (0.7 g). A pure light yellow solid was finally obtained through sublimation/purification. A yield was 89%.

Dopant 1: mass analysis (FAB) m/z 865 [(M+H)+]. 1H NMR (200 MHz, CDCl3): δ 8.21 (d, 4H, J=8.0 HZ), 7.89 (d, 4H, J=8.8 Hz), 7.76-7.52 (m, 6H), 7.46-7.12 (m, 6H), 7.01-6.54 (m, 16H)

Synthesis Example 2: Synthesis of Dopant 11

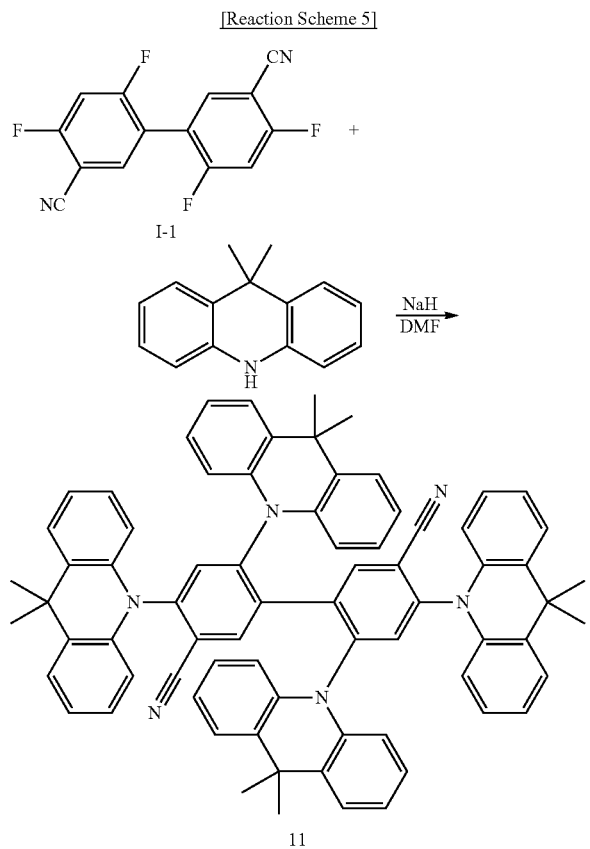

0.3 g of Dopant 11 was synthesized according to the same method as the method of Synthesis Example 1 except for using 9,9-dimethyl-9,10-dihydroacridine instead of 9H-carbazole. A pure light yellow solid was finally obtained through sublimation/purification. A yield was 80%.

Dopant 11: mass analysis (FAB) m/z 1033 [(M+H)+]. 1H NMR (200 MHz. CDCl3): δ 7.25 (s, 2H), 7.12-7.01 (m, 16H), 6.98-6.72 (m, 8H), 6.65-6.54 (m, 8H), 6.23 (s, 2H), 1.56 (s, 24H)

Synthesis Example 3: Synthesis of Dopant 2

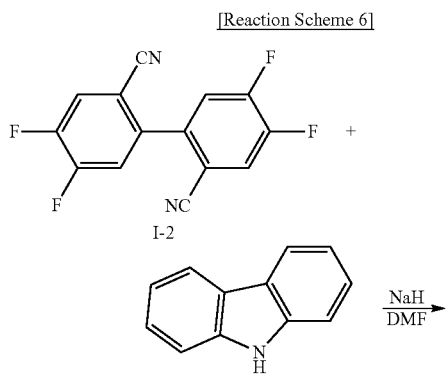

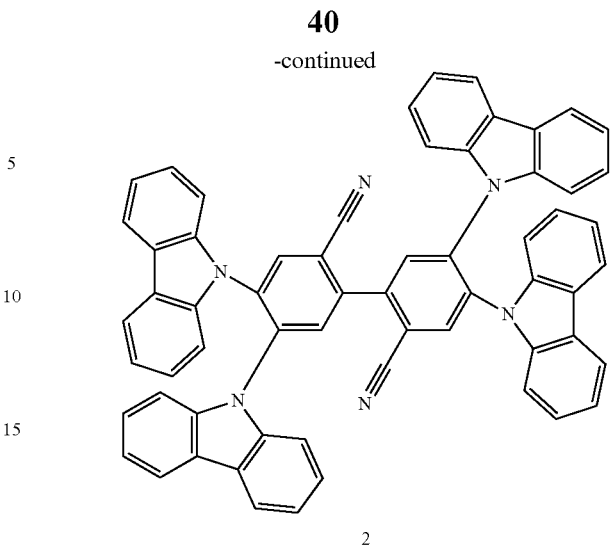

0.4 g of Dopant 2 was synthesized according to the same method as the method of Synthesis Example 1 except for using Intermediate I-2 instead of Intermediate I-1. A pure light yellow solid was finally obtained through sublimation/purification. A yield was 64%.

Dopant 2: mass analysis (FAB) m/z 865 [(M+H)+]. 1H NMR (200 MHz, CDCl3): δ 8.24 (d, 4H, J=8.2 Hz), 7.89 (s, 2H), 7.78-7.57 (m, 10H), 7.48-7.12 (m, 20H)

Synthesis Example 4: Synthesis of Dopant 9

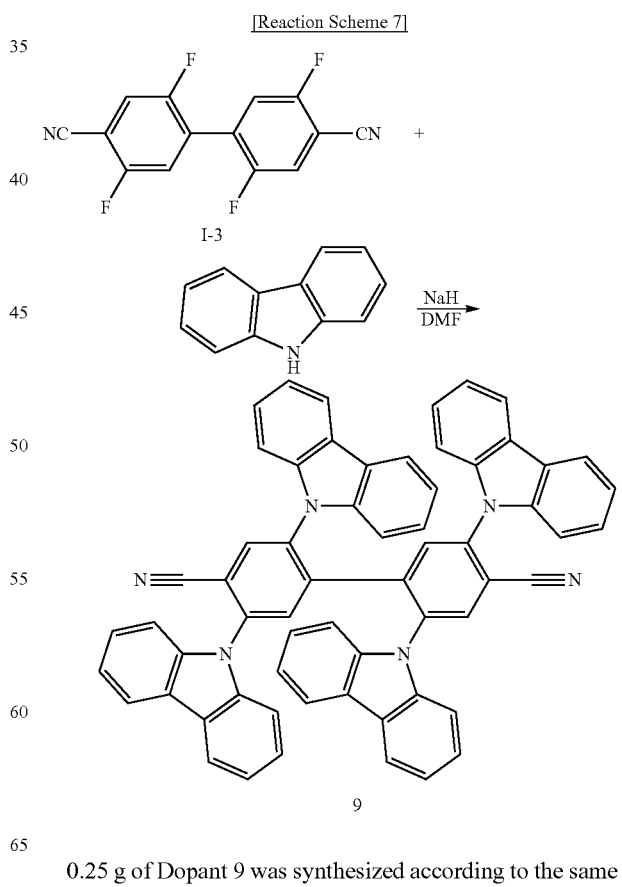

0.25 g of Dopant 9 was synthesized according to the same method as the method of Synthesis Example 1 except for using Intermediate I-3 instead of Intermediate I-1. A pure light yellow solid was finally obtained through sublimation/purification. A yield was 79%.

Dopant 9: mass analysis (FAB) m/z 865 [(M+H)+]. 1H NMR (200 MHz. CDC13): θ 8.29 (d, 4H, J=8.8 Hz), 8.12 (s, 2H), 7.87-7.67 (m, 10H), 7.62-7.20 (m, 20H), Synthesis Example 5: Synthesis of Dopant 21

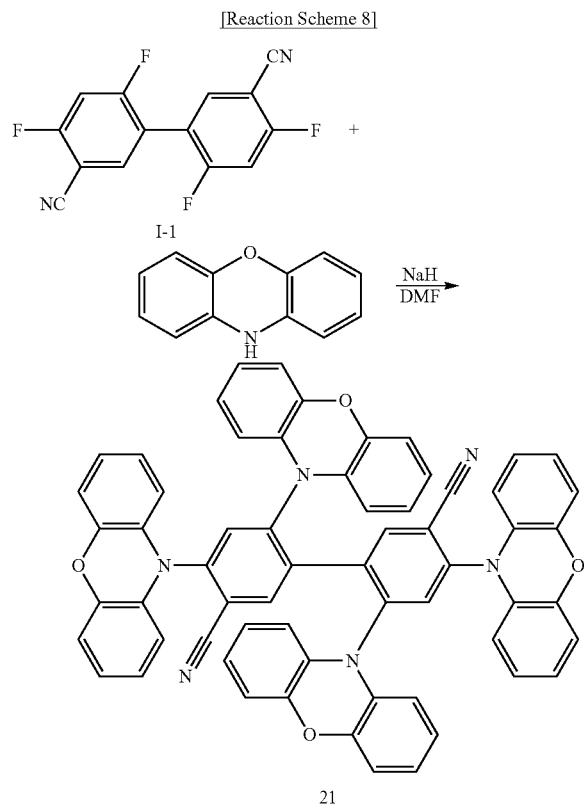

0.3 g of Dopant 21 was synthesized according to the same method as Synthesis Example 1 except for using 1 OH-phenoxazine instead of 9H-carbazole. A pure light yellow solid was finally obtained through sublimation/purification. A yield was 75%.

Evaluation 1

Energy levels of the dopants according to Synthesis Examples 1 to 4 were evaluated.

The energy levels of the dopants were measured by using an IVIUM equipment in a circulating voltage current method. An edge (1) of a graph obtained by coating a sample on a carbon electrode after dissolving tetrabutyl ammoniumperchloride in an acetonitrile solution and adjusting its concentration into 0.1 mole and then, changing a voltage in order of 0 V→3 V→0 V was measured. Then, an edge (2) of another graph obtained by changing the voltage in order of 0 V→-4 V→0 V was measured. HOMO energy (3) was obtained by using each measurement based on mCP as a reference value, subtracting each mCP measurement from 6.1, and adding (1) thereto, and bandgap energy (4) was obtained by (1)+(2). Then, LUMO energy (5) was obtained by (3)-(4). Herein, silver (Ag) was used as a reference electrode, platinum (Pt) was used as a counter electrode, and a carbon electrode was used as a working electrode.

Singlet energy was determined from a photoluminescence (PL) spectrum of a photoluminescent material by dispersing the photoluminescent material in polystyrene, and triplet energy was determined from a first phosphorescence peak of a low temperature PL spectrum.

The results are shown in Table 1.

TABLE 1

| | Maximum light-emitting wavelength ($\lambda_{max}$, nm) | Bandgap energy (eV) | $S^1$ (eV) | $T^1$ (eV) |
|---|---|---|---|---|
| Dopant 1 | 418 | 2.97 | 2.80 | 2.71 |
| Dopant 11 | 460 | 2.70 | 2.57 | 2.52 |
| Dopant 2 | 394 | 3.15 | 2.86 | 2.70 |
| Dopant 9 | 473 | 2.62 | 2.49 | 2.42 |

Referring to Table 1, the dopants according to Synthesis Examples 1 to 4 showed a maximum light-emitting wavelength ($\lambda_{max}$) in a range of about 380 to 580 nm, an energy bandgap in a range of about 2.5 to 3.5 eV, and an energy gap ($|S^1-T^1|$) between singlet energy and triplet energy in a range of 0.05 to 0.20 eV. Accordingly, the dopants according to Synthesis Examples 1 to 4 turned out to advantageously work for a reversed intersystem crossing of excitons into blue light fluorescent emission.

Evaluation 2

Each distortion angle of the dopants according to Synthesis Examples 1 to 4 was calculated by using Gaussian09, and the results are shown in Table 2.

TABLE 2

| | Distortion angle (°) |
|---|---|
| Dopant 1 | 48 |
| Dopant 11 | 51 |
| Dopant 2 | 58 |
| Dopant 9 | 50 |

Referring to Table 2, an electron cloud distribution of HOMO energy and LUMO energy and a difference between singlet energy and triplet energy may be adjusted by using a steric hindrance effect of substituents at an ortho position in the biphenyl core of each dopant and adjusting the number of substituents of electron donating groups and electron withdrawing groups. Accordingly, a dopant having high color purity may be synthesized by narrowing a full width at half maximum (FWHM).

Manufacture of Organic Light Emitting Diode

Example 1

Each thin film was vacuum-deposited under a vacuum degree of $5.0 \times 10^{-4}$ Pa on a glass substrate on which 100 nm-thick ITO was laminated. First, PEDOT:PSS (Sigma Aldrich, 60 nm), TAPC (4,4'-cyclohexylidenebis[N,N-bis(4-methylphenyl)benzenamine], EM INDEX, 10 nm), TCTA (4,4',4''-tris(carbazol-9-yl)-triphenylamine, EM INDEX, 10 nm), and mCP (1,3-bis(N-carbazolyl)benzene, EM INDEX, 10 nm) were sequentially formed on the ITO. Subsequently, a mixed host, mCP and DPEPO (bis(2-(diphenylphosphino)phenyl)ether oxide, nm) and Dopant 1 obtained in Synthesis Example 1 were co-deposited to form a 25 nm-thick light emitting layer. Herein, Dopant 1 was set to be 5.0 wt % based on a total amount of the light emitting layer. Subsequently, TSP01 (diphenyl-4-triphenylsilylphenyl-phosphine oxide, P&H Tech, 20-40 nm), TPBi (1,3,5-tris(1-phenyl-1H- benzimidazol-2-yl)benzene, EM INDEX, 30 nm) were sequentially formed, and then lithium fluoride (LiF, 0.8 nm) was vacuum-deposited and an aluminum (Al) cathode (100 nm) was formed to manufacture an organic light emitting diode.

Each organic light emitting diode was manufactured by fixing a doping concentration at 5% but changing a thickness of TSP01 into 20, 30, and 40 nm. An organic light emitting diode manufactured by using Compound 1 was optimized when TSPO1 had a thickness of 30 nm and showed maximum quantum efficiency of 14.02% and a color coordinate of deep blue (0.14, 0.12).

The results depending on a thickness of TSP01 are shown in Table 3.

TABLE 3

| TSPO1 thickness | Color coordinate (x, y) | Maximum quantum efficiency | Maximum power efficiency | Maximum current efficiency |
|---|---|---|---|---|
| 20 nm | 0.14, 0.10 | 10.07% | 8.38 lm/w | 9.34 cd/A |
| 30 nm | 0.14, 0.12 | 14.02% | 10.20 lm/w | 14.13 cd/A |
| 40 nm | 0.14, 0.16 | 8.45% | 9.42 lm/w | 10.50 cd/A |

Example 2

Organic light emitting diodes were manufactured according to the same method as Example 1 except for using Dopant 11 of Synthesis Example 2 instead of Dopant 1 but changing a doping concentration into 1%, 3%, and 5% and using TSP01 to have a thickness of 30 nm.

The organic light emitting diodes according to each doping concentration of 1, 3, and 5% showed maximum quantum efficiency of 20.12% and a color coordinate (0.18 and 0.37).

The results are shown in Table 4.

TABLE 4

| Doping concentration | Color coordinate (x, y) | Maximum quantum efficiency | Maximum Power efficiency | Maximum current efficiency |
|---|---|---|---|---|
| 1% | 0.18, 0.37 | 20.12% | 34.08 lm/w | 43.39 cd/A |
| 3% | 0.18, 0.37 | 19.01% | 34.63 lm/w | 41.15 cd/A |
| 5% | 0.18, 0.37 | 19.37% | 34.05 lm/w | 43.46 cd/A |

Example 3

Each thin film was vacuum-deposited under a vacuum degree of $5.0 \times 10^{-4}$ Pa on a glass substrate on which 100 nm-thick ITO was laminated. First, PEDOT:PSS (Sigma Aldrich, 60 nm), TAPC, and mCP were sequentially formed on ITO. Subsequently, a mixed host, mCP (1,3-bis(N-carbazolyl)benzene, EM INDEX, 10 nm) and DPEPO (25 nm) and Dopant 2 obtained in Synthesis Example 3 were co-deposited to form a 25 nm-thick light emitting layer. Then TSP01 and TPBi (30 nm) were sequentially formed, lithium fluoride (LiF) (0.8 nm) was vacuum-deposited, and an aluminum (Al) cathode (100 nm) was formed to manufacture an organic light emitting diode. An organic light emitting diode was manufactured by fixing the doping concentration at 5% but a thickness of an electron transport layer (ETL) (TSPO1) into and 30 nm. An organic light emitting diode manufactured by using Compound 3 showed maximum quantum efficiency of 4.78% and a color coordinate (0.16 and 0.13).

The results are shown in Table 5.

TABLE 5

| Thickness of electron transport layer | Color coordinate (x, y) | Maximum quantum efficiency | Maximum Power efficiency | Maximum current efficiency |
|---|---|---|---|---|
| 20 nm | 0.16, 0.14 | 4.11% | 4.57 lm/w | 5.48 cd/A |
| 30 nm | 0.16, 0.13 | 4.78% | 4.79 lm/w | 6.10 cd/A |

Evaluation 3

Optical characteristics and efficiency of the organic light emitting diodes according to Examples 1 to 3 were evaluated by using a semiconductor parameter•analyzer (Agilent Technologies: E5273A), an optical power meter-measuring device (Neport Corp.: 1930 C), and an optical spectrometer (Daeyang Optical Co., Ltd.: USB2000).

The results are shown in Table 6.

TABLE 6

| | Color coordinate | Full width at half maximum (FWHM) (nm) | EQE (%) |
|---|---|---|---|
| Example 1 | 0.14, 0.12 | 48 | 14.02 |
| Example 2 | 0.18, 0.37 | 71 | 20.12 |
| Example 3 | 0.16, 0.13 | 78 | 4.78 |

Referring to Table 6, the organic light emitting diodes according to Exampled 1 to 3 had a sufficient light-emitting full width at half maximum (FWHM) of less than or equal to about nm in a blue wavelength region and emitted blue light with high purity.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: anode
120: cathode
130: light emitting layer

The invention claimed is:
1. A dopant for an organic optoelectronic device represented by Chemical Formula 1:

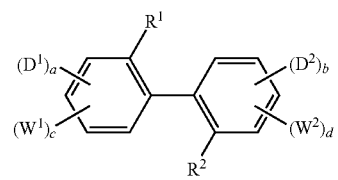

[Chemical Formula 1]

wherein, in Chemical Formula 1,
$W^1$ and $W^2$ are independently a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; or a combination thereof, $D^1$ and $D^2$ are independently a group represented by Chemical Formula 2, $R^1$ and $R^2$ are independently a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; a combination thereof; or a group represented by Chemical Formula 2, and a, b, c, and d are integers satisfying $0 \leq a+b \leq 4$ and $0 \leq c+d \leq 2$, provided that a+b and c+d are not 0 simultaneously,

[Chemical Formula 2]

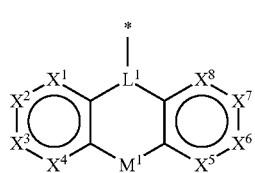

wherein, in Chemical Formula 2, $X^1$ to $X^8$ are independently N or $CR^a$, $L^1$ is N, B, C, $CR^b$, or $SiR^c$, $M^1$ is a single bond, $CR^dR^e$, $SiR^fR^g$, $NR^h$, O, or S, $R^a$ is hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group or a substituted or unsubstituted C3 to C30 heterocyclic group, $R^b$ to $R^h$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, and

* is a linking point with Chemical Formula 1.

2. The dopant for an organic optoelectronic device of claim 1, wherein $R^1$ is the same as $W^1$ or $D^1$ and $R^2$ is the same as $W^2$ or $D^2$.

3. The dopant for an organic optoelectronic device of claim 2, wherein the dopant is represented by one of Chemical Formulae 1-I to 1-IV:

[Chemical Formula 1-I]

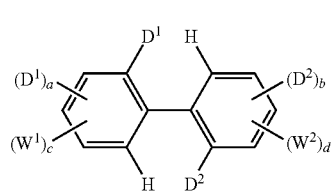

[Chemical Formula 1-II]

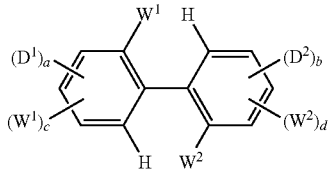

[Chemical Formula 1-III]

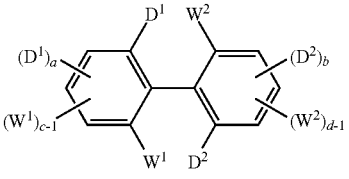

[Chemical Formula 1-IV]

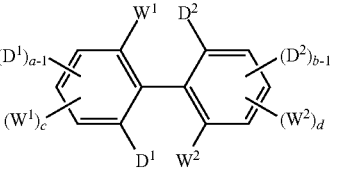

wherein, in Chemical Formulae 1-1 to 1-IV, $W^1$ and $W^2$ are independently a cyano group; a nitro group; an amide group; sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; or a combination thereof, $D^1$ and $D^2$ are independently a group represented by the Chemical Formula 2, and a, b, c, and d are integers satisfying $0 \le a+b \le 4$ and $0 \le c+d \le 2$, provided that a+b and c+d are not 0 simultaneously.

4. The dopant for an organic optoelectronic device of claim 3, wherein each of $D^1$ and $W^1$ and $D^2$ and $W^2$ are linked in an ortho position or each of two $D^1$'s and two $D^2$'s are linked in an ortho position.

5. The dopant for an organic optoelectronic device of claim 3, wherein the total number of $D^1$ and $D^2$ is 3 to 5 and the total number of $W^1$ and $W^2$ is 1 to 3.

6. The dopant for an organic optoelectronic device of claim 1, wherein Chemical Formula 2 is represented by one of Chemical Formulae 2-I to 2-VI:

[Chemical Formula 2-I]

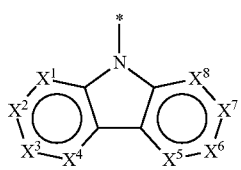

[Chemical Formula 2-II]

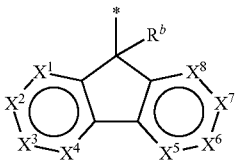

[Chemical Formula 2-III]

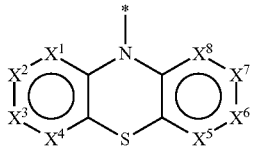

[Chemical Formula 2-IV]

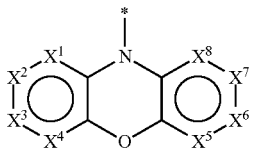

[Chemical Formula 2-V]

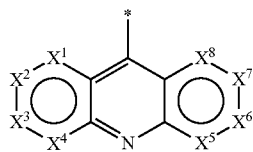

-continued

[Chemical Formula 2-VI]

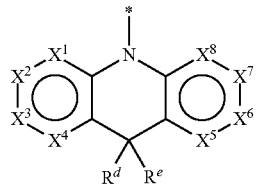

wherein, in Chemical Formulae 2-I to 2-VI, $X^1$ to $X^8$ are independently N or $CR^a$, $R^a$ is hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group or a substituted or unsubstituted C3 to C30 heterocyclic group, $R^b$, $R^d$, and $R^e$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, and * is a linking point with Chemical Formula 1.

7. The dopant for an organic optoelectronic device of claim 1, wherein two phenyl groups of Chemical Formula 1 are distorted to have an angle of 30 degrees to 70 degrees.

8. The dopant for an organic optoelectronic device of claim 1, wherein the dopant is a fluorescent dopant having a maximum light-emitting wavelength ($\lambda_{max}$) of 380 nm to 580 nm.

9. The dopant for an organic optoelectronic device of claim 1, wherein the dopant is a fluorescent dopant having an energy gap between singlet energy and triplet energy of less than or equal to 0.2 eV.

10. The dopant for an organic optoelectronic device of claim 1, wherein the dopant represented by Chemical Formula 1 is one of compounds of Group 1:

[Group 1]
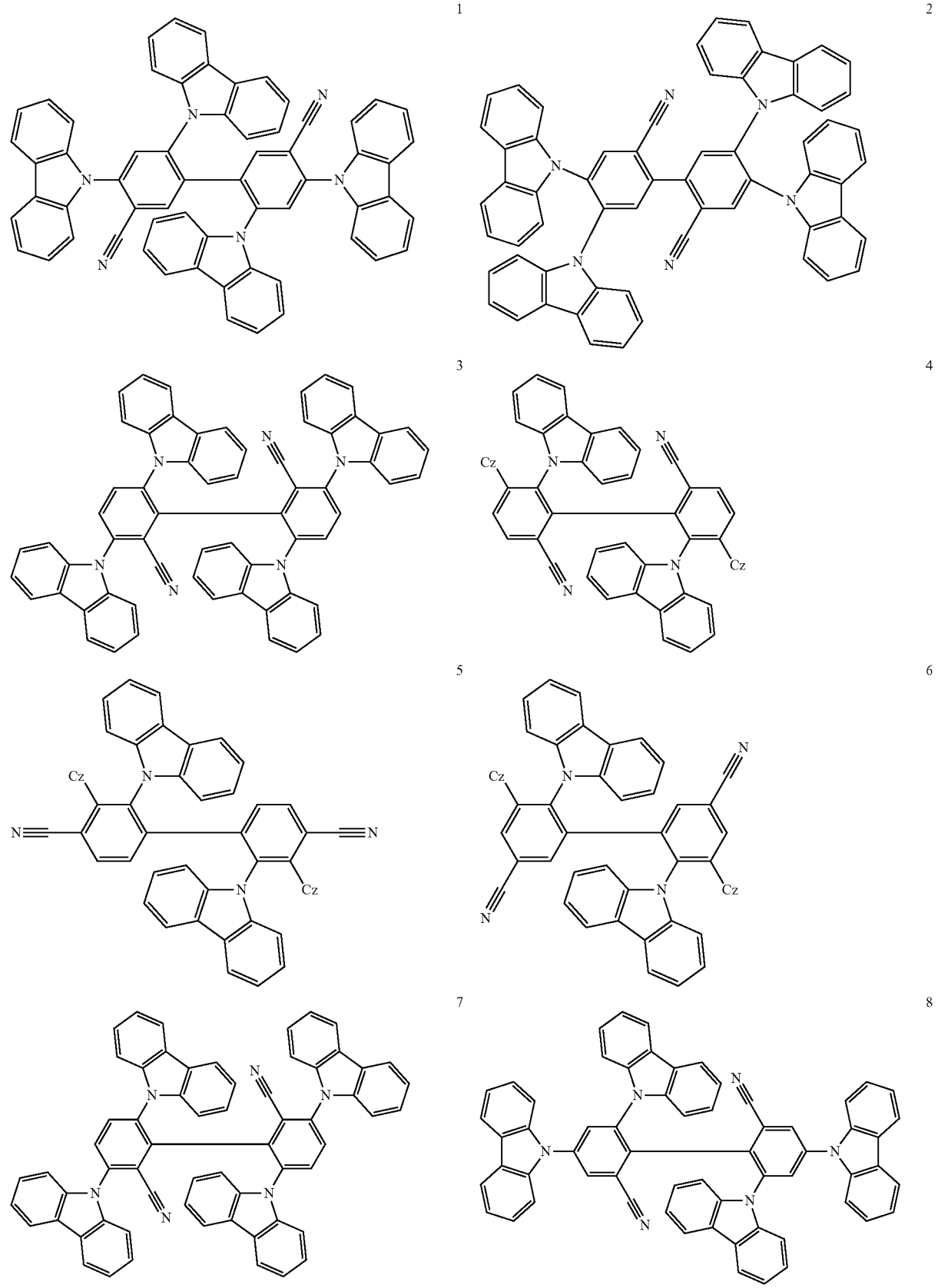

-continued
9
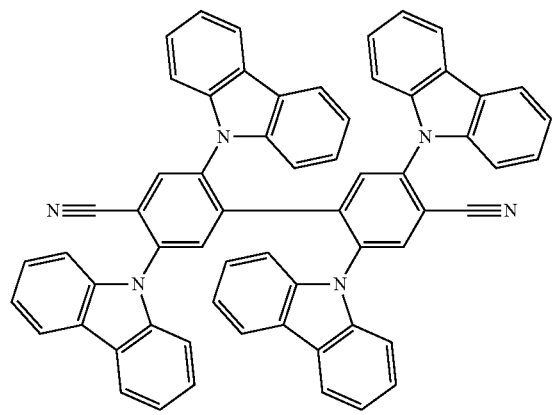
10
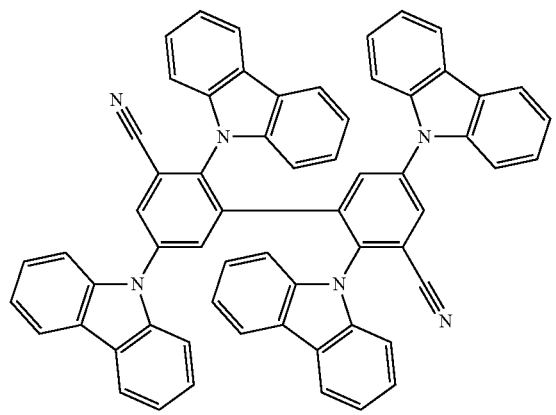
11
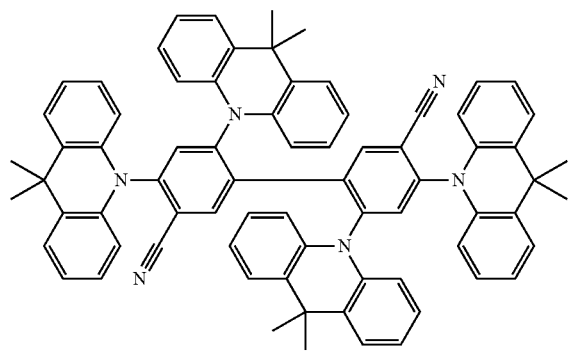
12
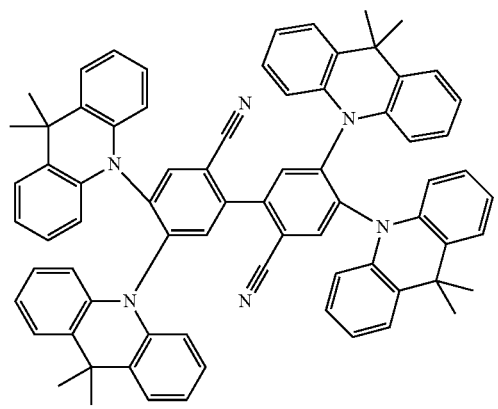
13
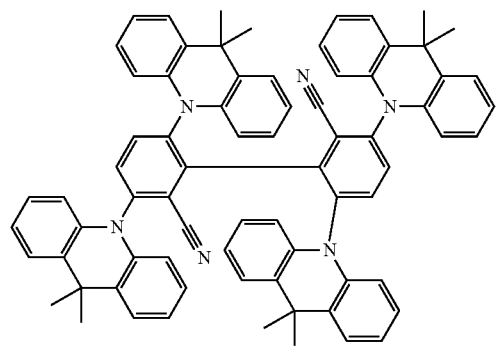
14
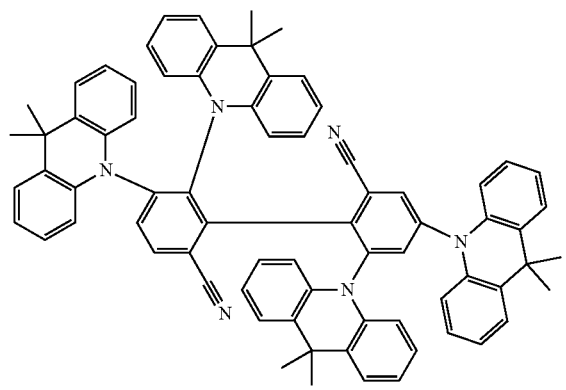
15
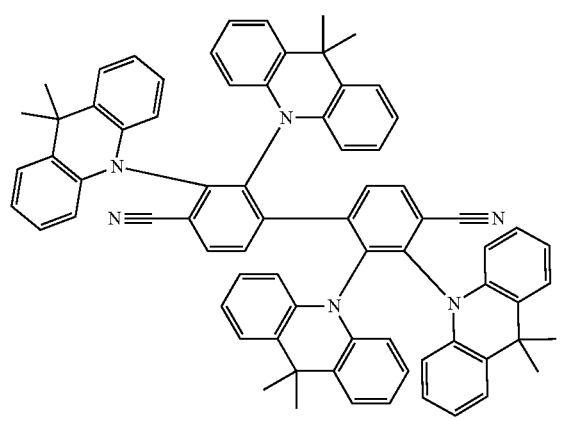
16
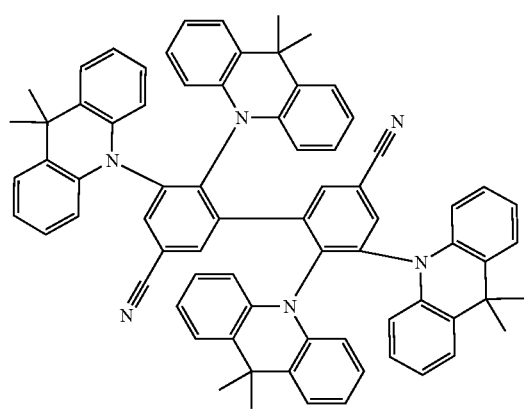

-continued
17
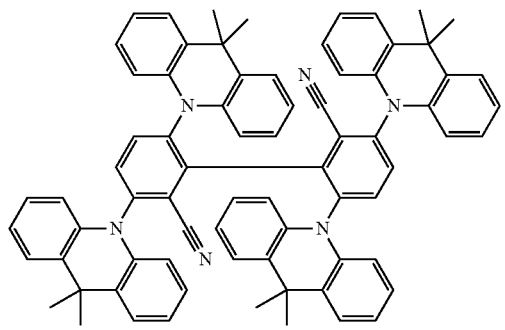
18
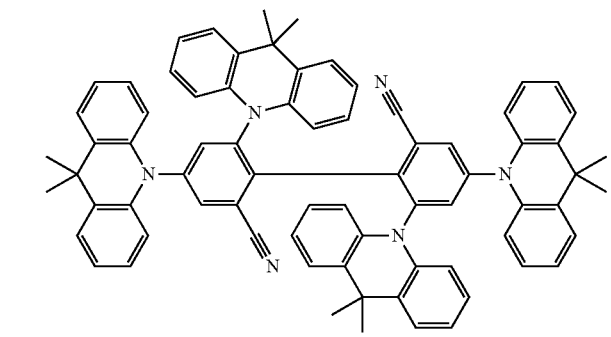
19
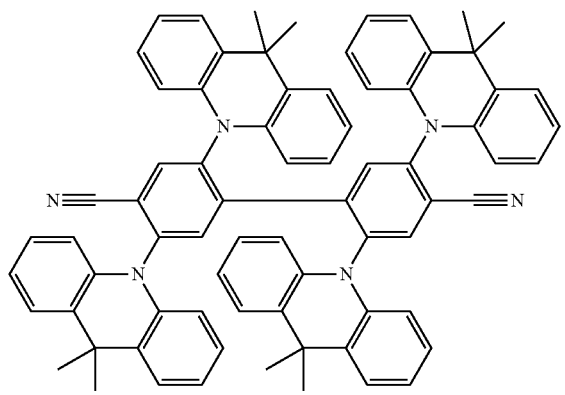
20
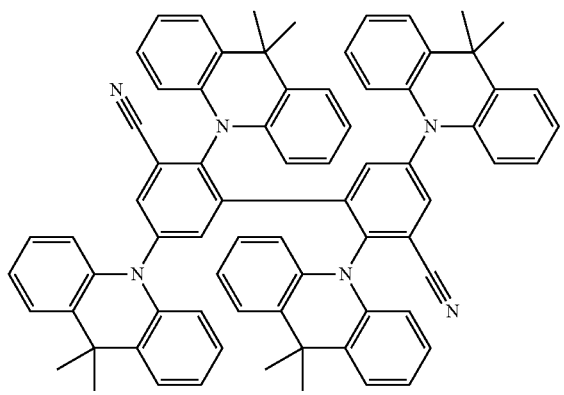
21
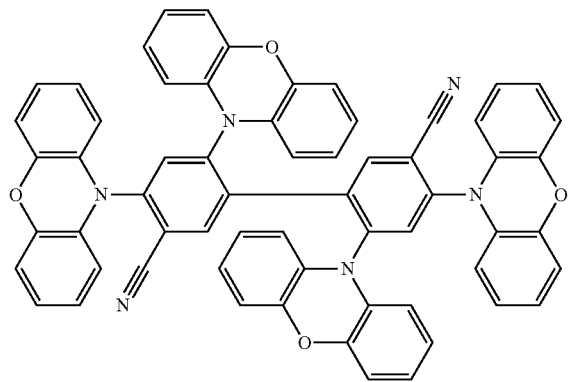
22
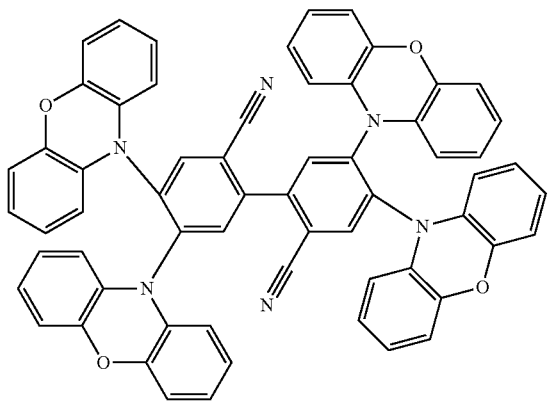
23
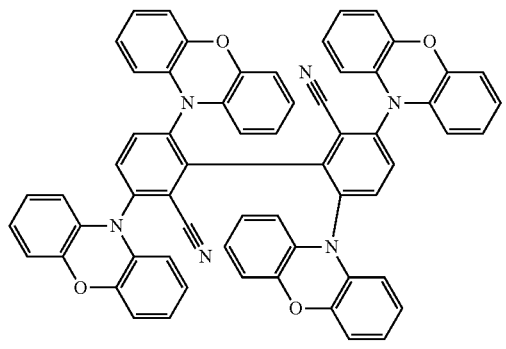
24
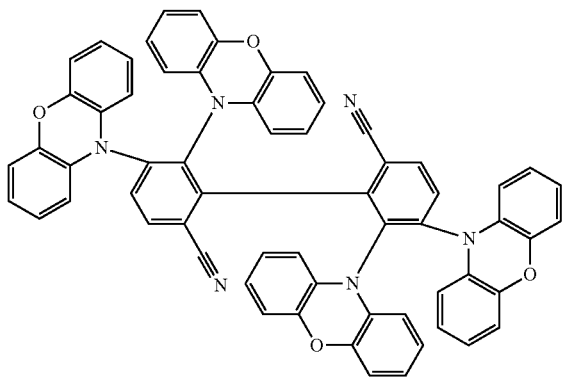

-continued
25
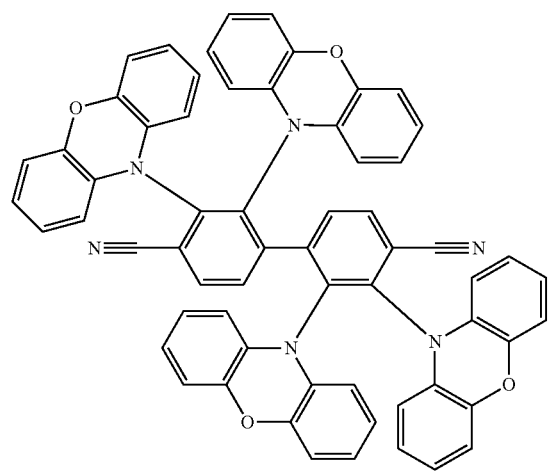
26
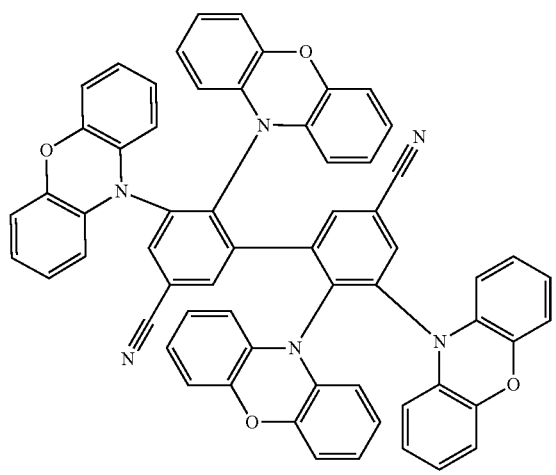
27
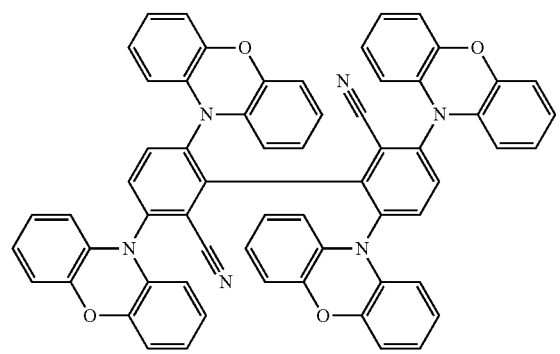
28
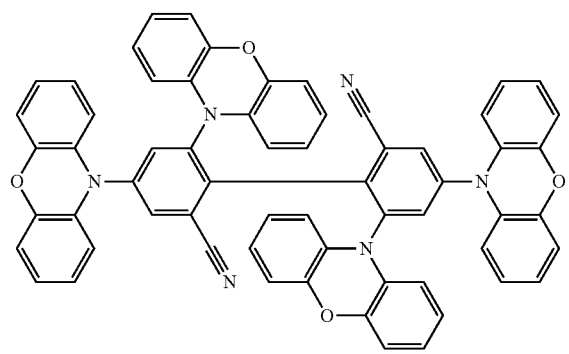
29
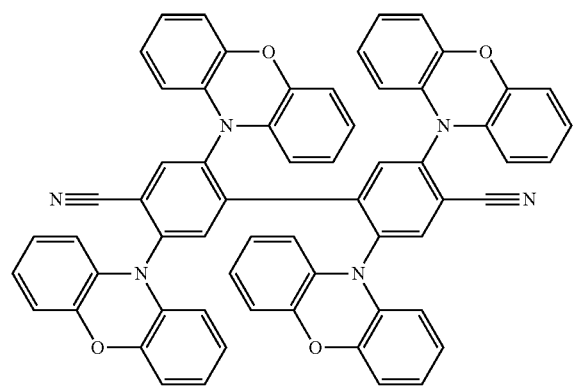
30
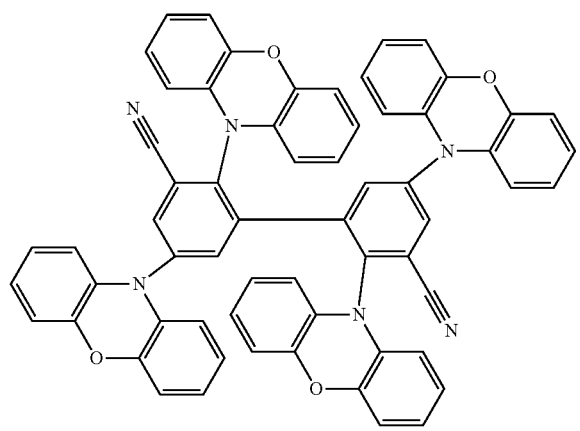

-continued
31
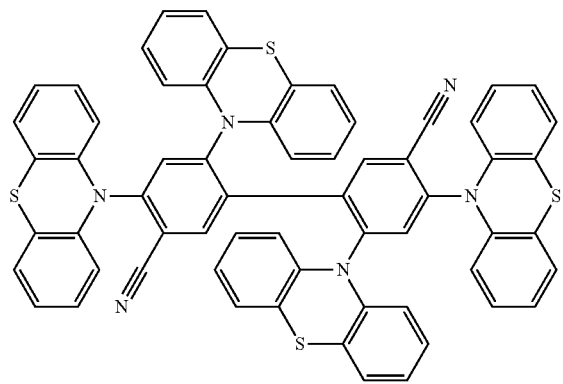
32
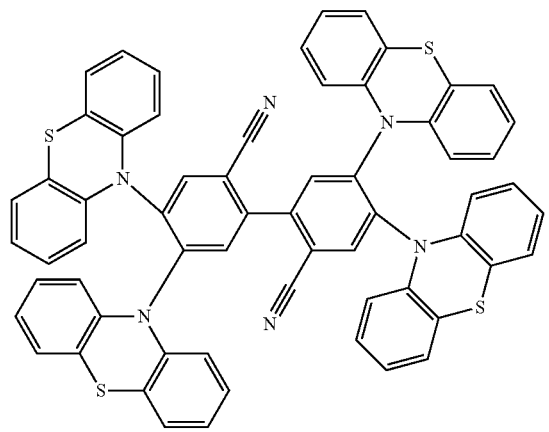
33
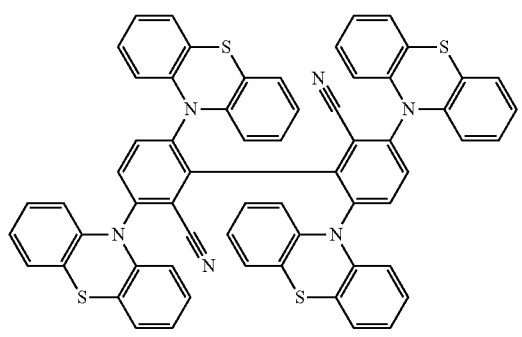
34
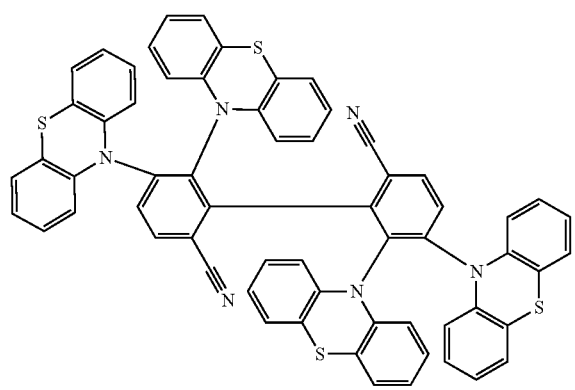
35
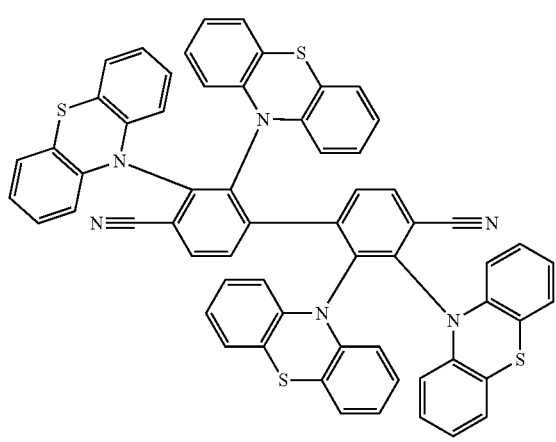
36
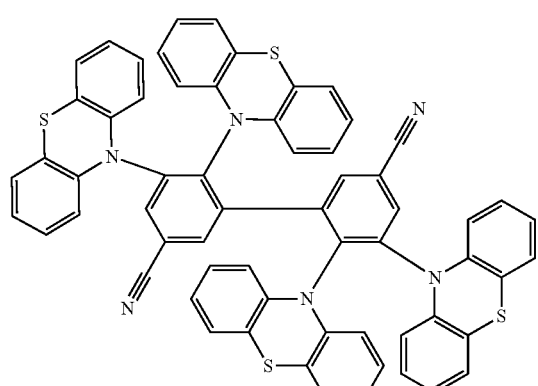

-continued
37
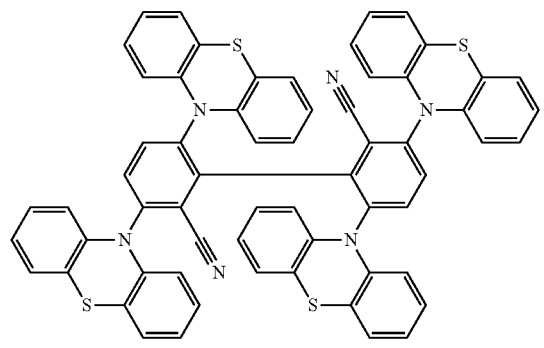
38
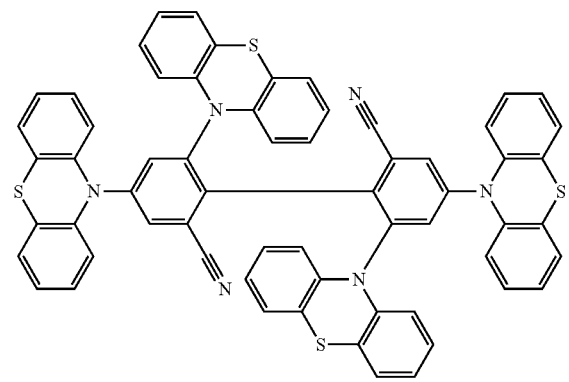
39
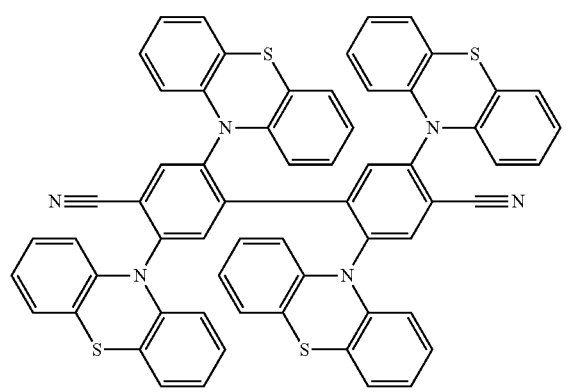
40
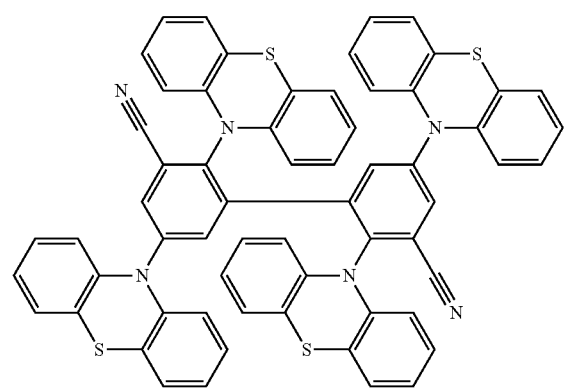
41
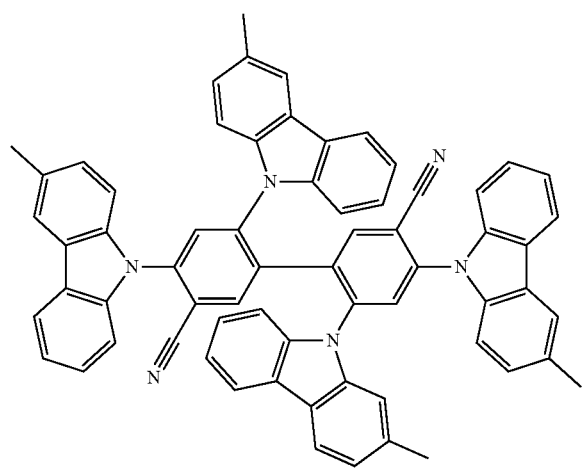
42
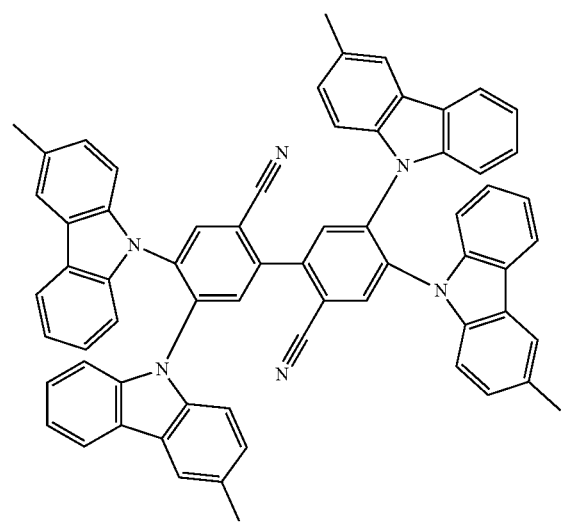

43
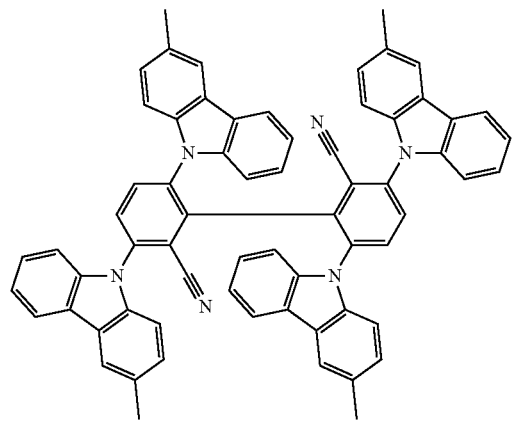
44
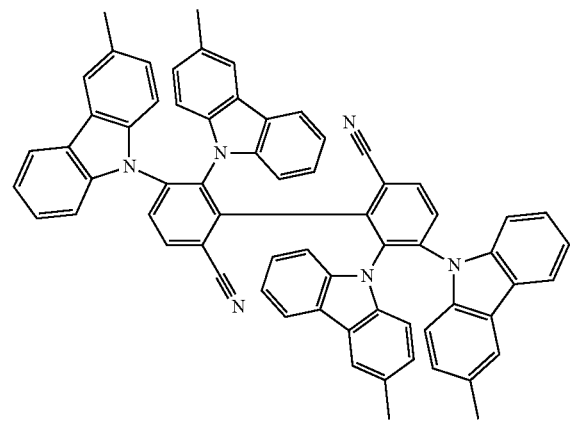
45
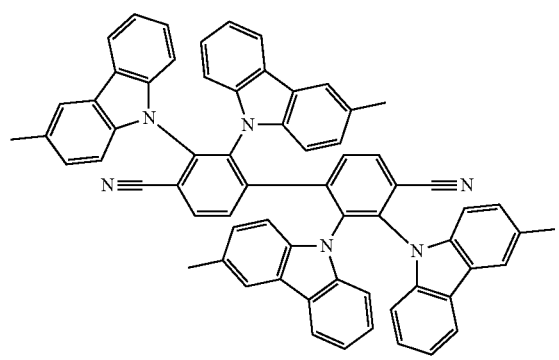
46
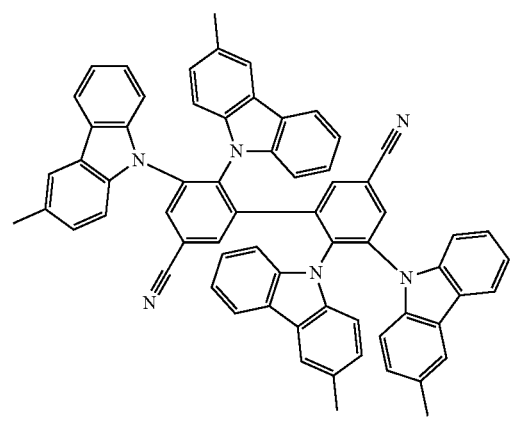
47
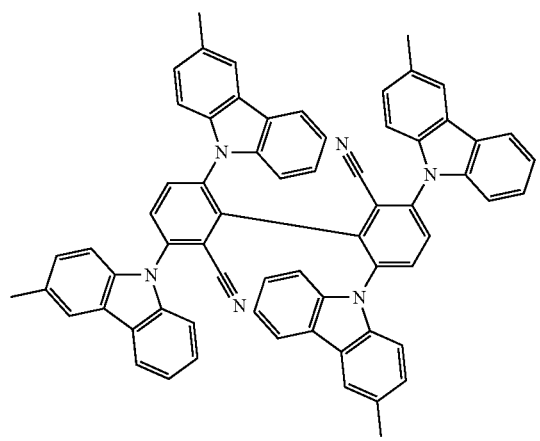
48
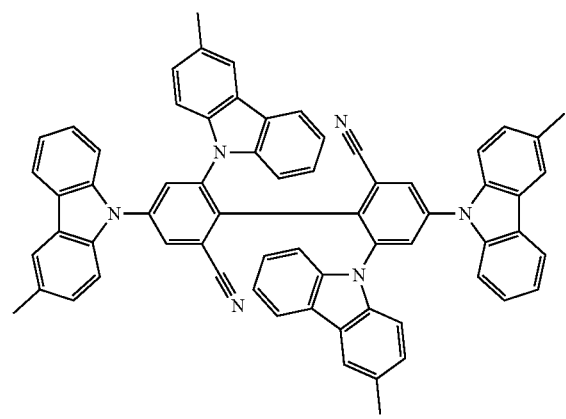

49
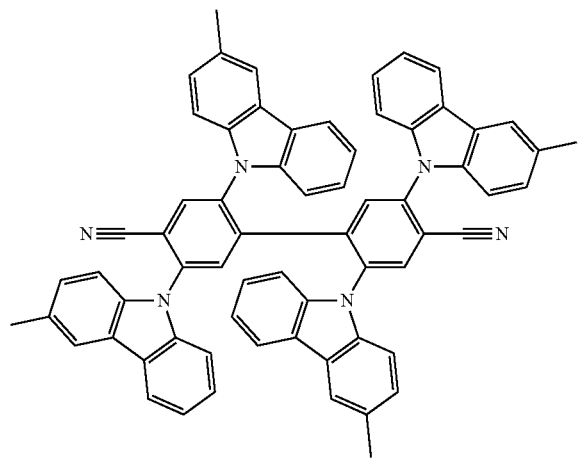
50
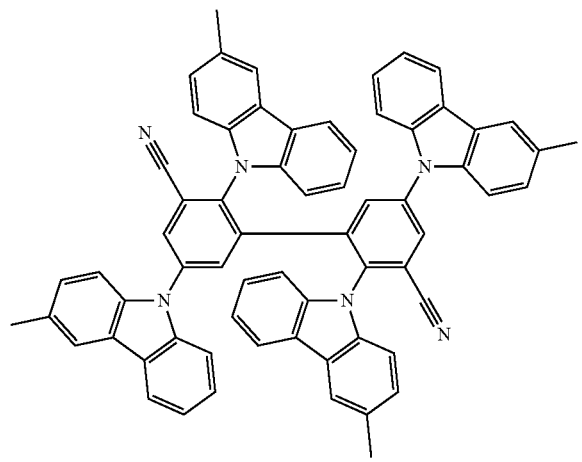
51
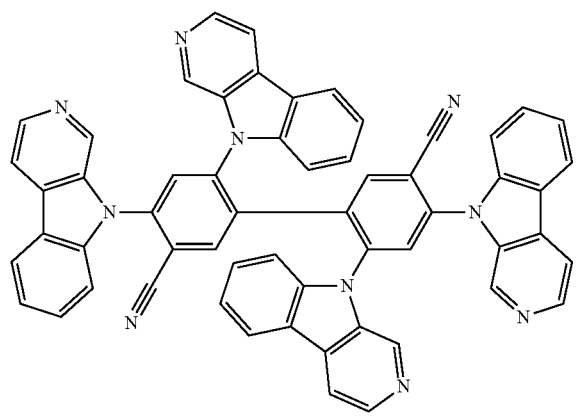
52
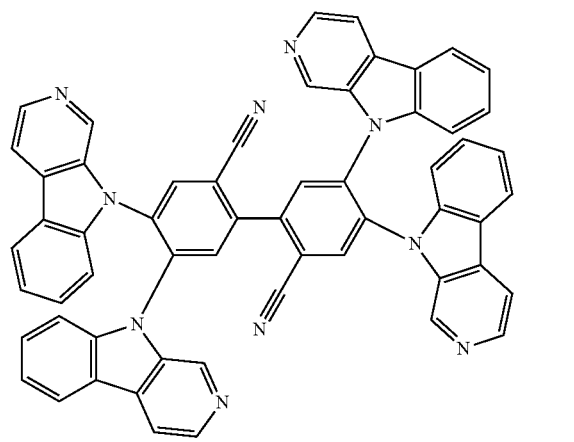
53
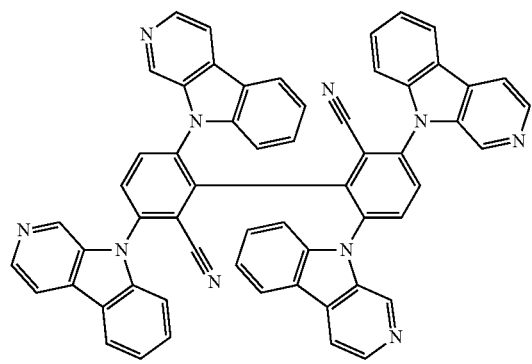
54
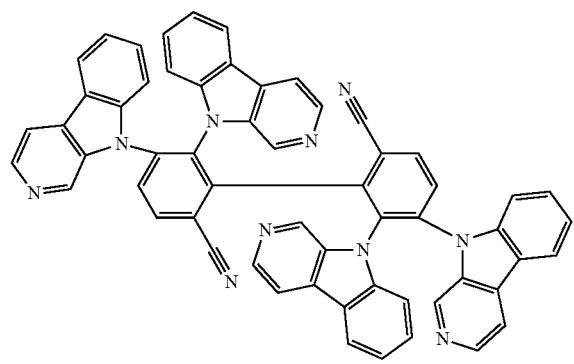

55
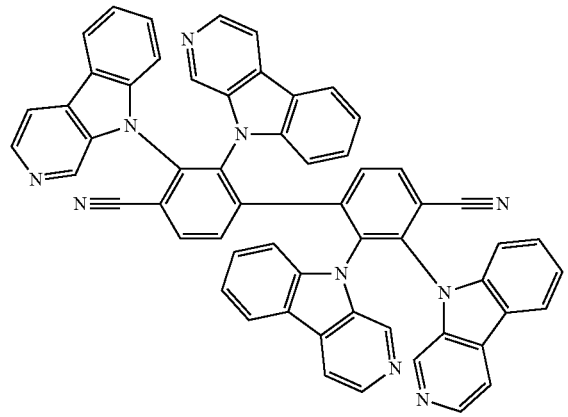
56
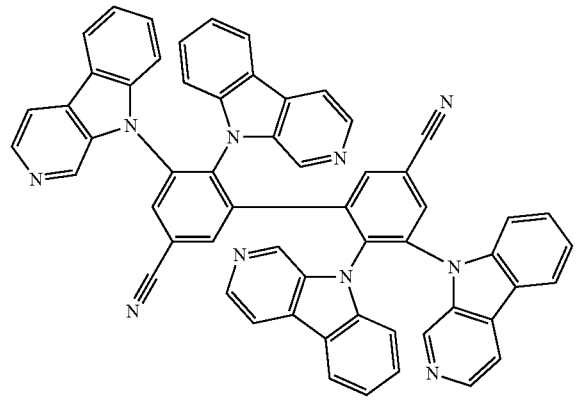
57
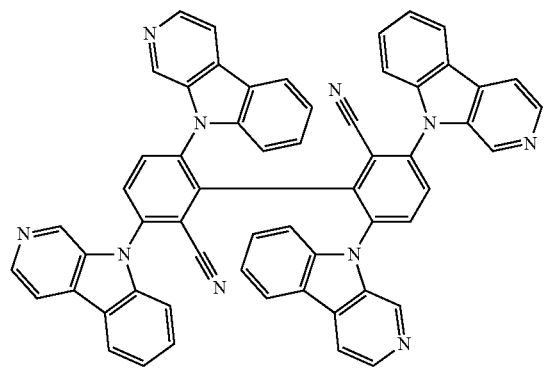
58
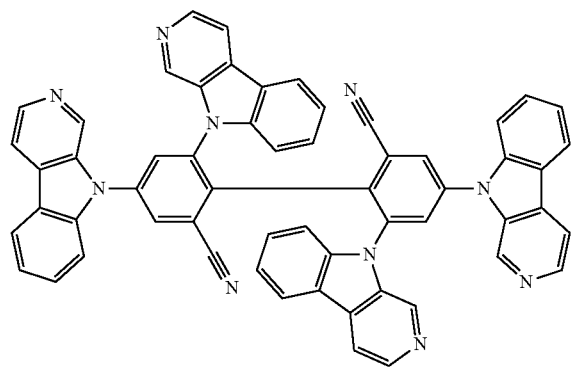
59
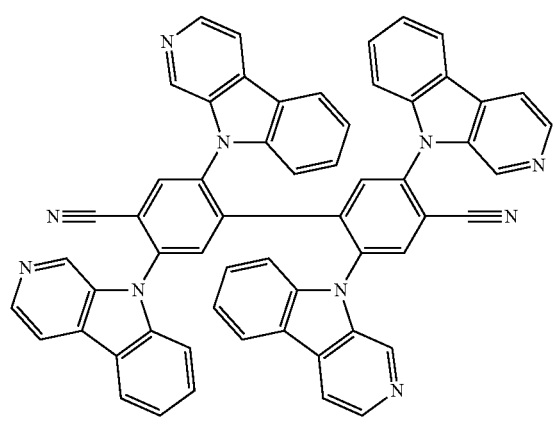
60
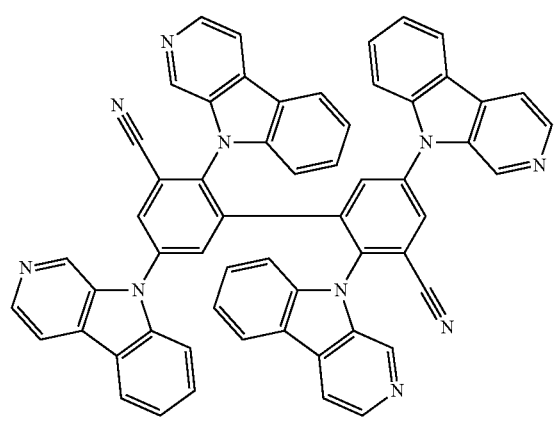

-continued
61
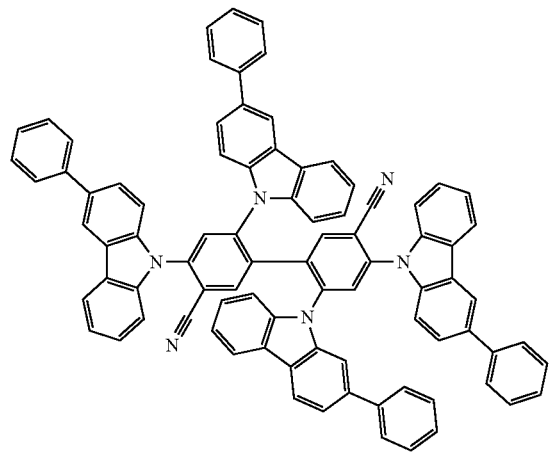
62
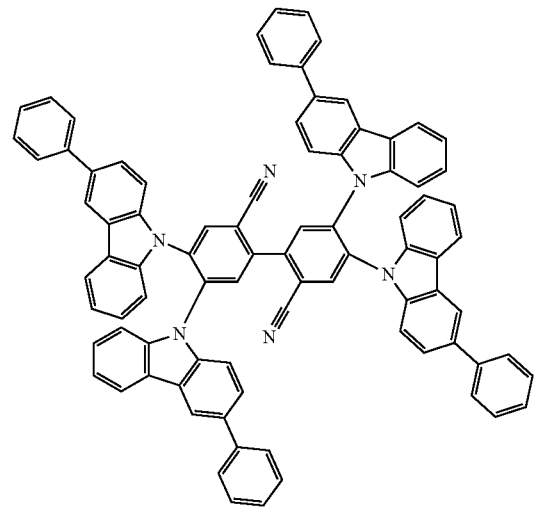
63
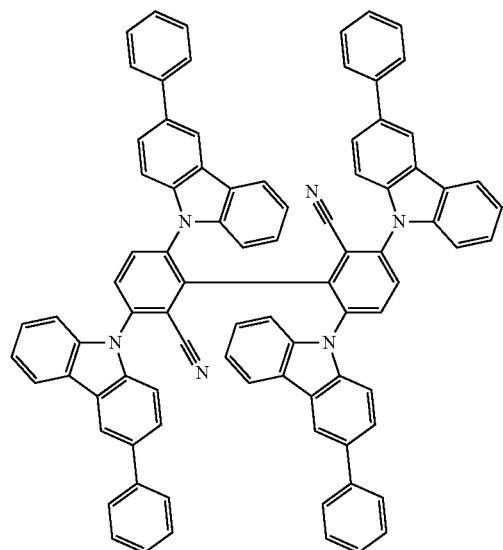
64
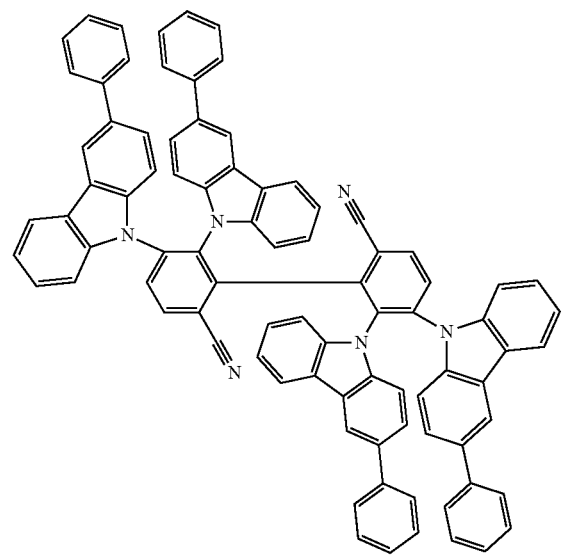
65
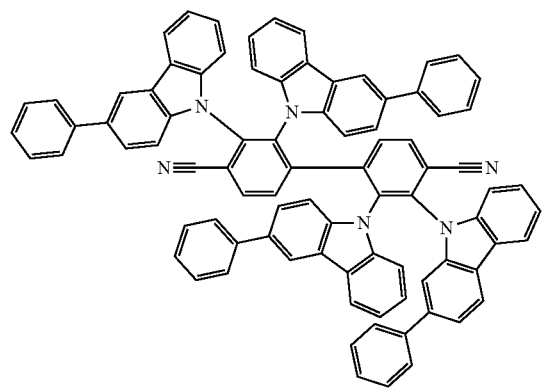
66
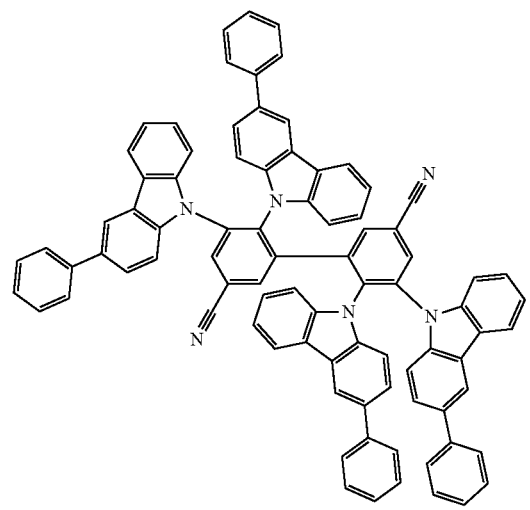

67
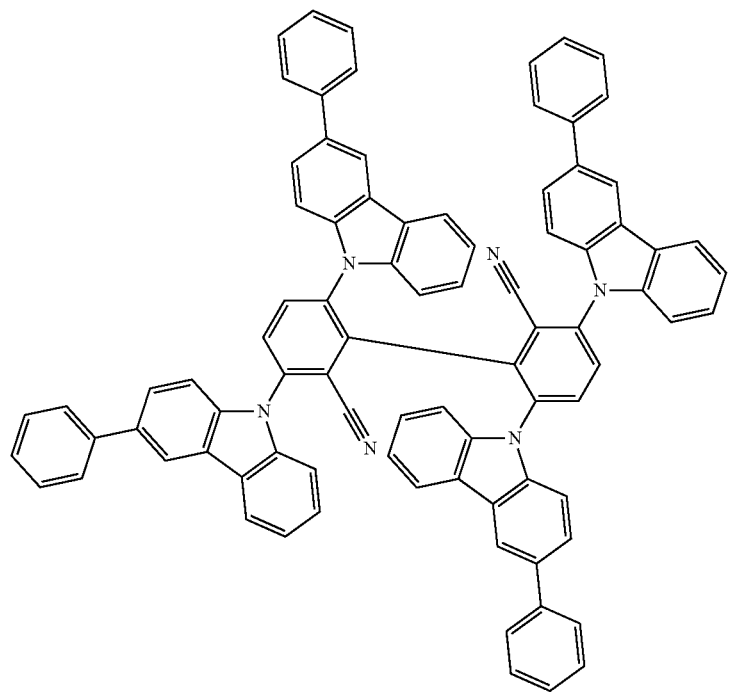
68
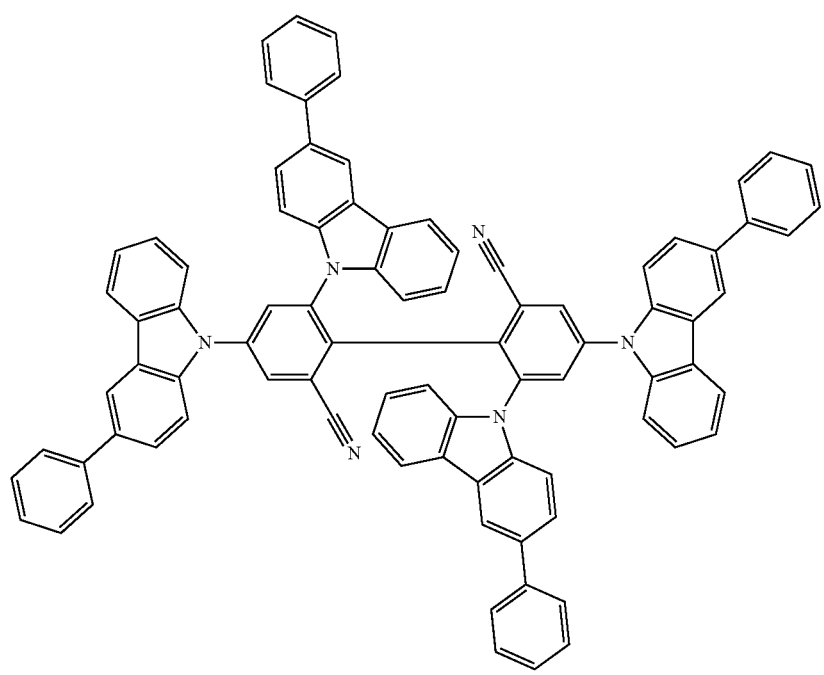

-continued

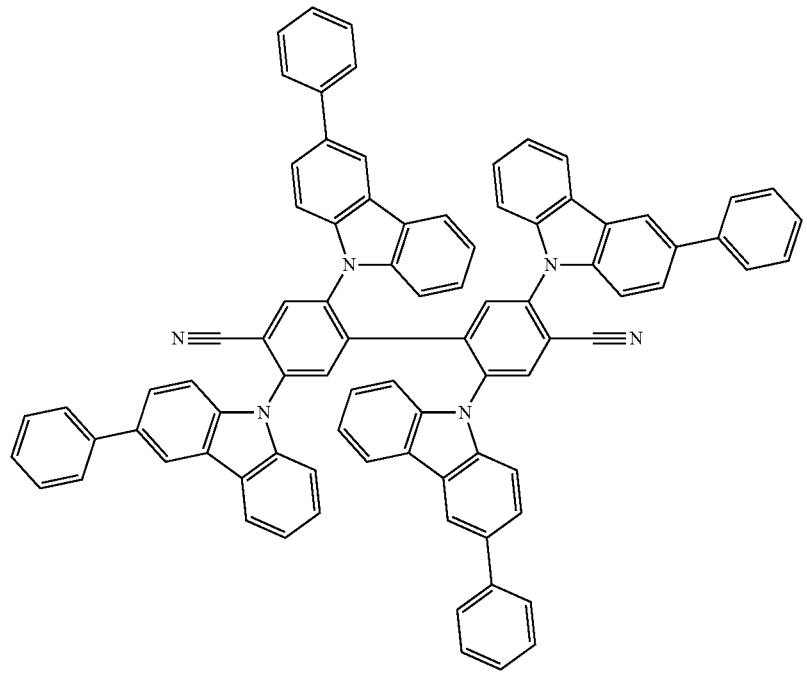
69

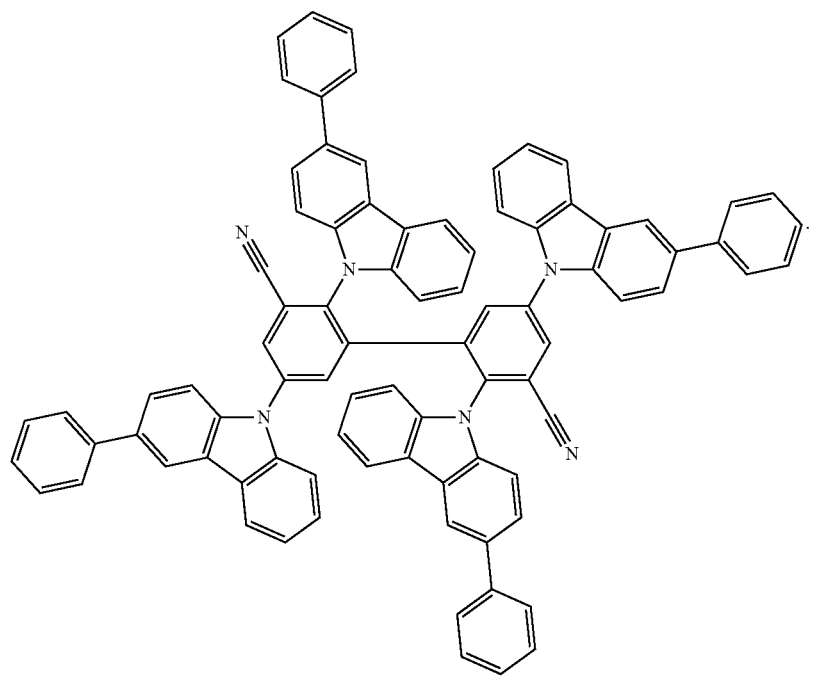
70

11. An organic optoelectronic device, comprising
an anode and a cathode facing each other, and
an organic layer between the anode and the cathode
wherein the organic layer includes
at least one host, and
the dopant of claim 1.

12. The organic optoelectronic device of claim 11, wherein the dopant is a fluorescent dopant having a maximum light-emitting wavelength ($\lambda_{max}$) in 380 nm to 580 nm.

13. The organic optoelectronic device of claim 11, wherein the host is selected from compounds having a larger energy bandgap between HOMO and LUMO than the dopant.

14. The organic optoelectronic device of claim 11, wherein the dopant is included in an amount of 0.01 wt % to 40 wt % based on a total amount of the host and the dopant.

15. The organic optoelectronic device of claim 11, wherein the organic optoelectronic device has a light-emitting full width at half maximum (FWHM) of 10 nm to 100 nm.

16. A display device comprising the organic optoelectronic device of claim 11.

\* \* \* \* \*